United States Patent
Jimenez, Jr. et al.

(10) Patent No.: US 12,318,318 B2
(45) Date of Patent: *Jun. 3, 2025

(54) DELIVERY SYSTEMS FOR STENTS HAVING PROTRUDING FEATURES

(71) Applicant: ReFlow Medical, Inc., San Clemente, CA (US)

(72) Inventors: Teodoro S. Jimenez, Jr., Aliso Viejo, CA (US); Patrick Lo, Diamond Bar, CA (US); John Fulkerson, Rancho Santa Margarita, CA (US); Isa Rizk, San Diego, CA (US); Francisco Aguayo, Hemet, CA (US); Jihad Ali Mustapha, Ada, MI (US); Gary Ansel, Columbus, OH (US)

(73) Assignee: ReFlow Medical, Inc., San Clemente, CA (US)

( * ) Notice: Subject to any disclaimer, the term of this patent is extended or adjusted under 35 U.S.C. 154(b) by 88 days.

This patent is subject to a terminal disclaimer.

(21) Appl. No.: 18/135,034

(22) Filed: Apr. 14, 2023

(65) Prior Publication Data
US 2023/0248558 A1     Aug. 10, 2023

Related U.S. Application Data

(62) Division of application No. 16/593,842, filed on Oct. 4, 2019, now Pat. No. 11,648,139.
(Continued)

(51) Int. Cl.
*A61F 2/966*     (2013.01)
*A61F 2/958*     (2013.01)
(Continued)

(52) U.S. Cl.
CPC ............ *A61F 2/966* (2013.01); *A61F 2/958* (2013.01); *A61F 2002/0081* (2013.01);
(Continued)

(58) Field of Classification Search
None
See application file for complete search history.

(56) References Cited

U.S. PATENT DOCUMENTS

| 6,425,915 B1 | 7/2002 | Khosravi et al. |
| 6,991,617 B2 | 1/2006 | Hektner et al. |
| (Continued) | | |

FOREIGN PATENT DOCUMENTS

| CN | 101933855 | 1/2011 |
| CN | 102098988 | 6/2011 |
| (Continued) | | |

OTHER PUBLICATIONS

International Search Report and Written Opinion from PCT/US2019/054847, dated Mar. 23, 2020, 17 pages.
(Continued)

*Primary Examiner* — Rebecca S Preston
(74) *Attorney, Agent, or Firm* — BAKERHOSTETLER

(57) ABSTRACT

Delivery systems for expandable elements, such as stents or scaffolds having spikes, flails, or other protruding features for penetrating target tissue and/or delivering drugs within a human patient are described along with associated methods for using such systems. The delivery systems can be provided with a stent that is positioned over an inflatable balloon for expansion and delivery of the stent to a target delivery location. By positioning the stent over and about the inflatable balloon, the stent is ready to be expanded by the balloon immediately upon unsheathing with respect to the outer shaft. Additionally or alternatively, a stent can be positioned in an axially offset arrangement with respect to a balloon to reduce the need for space required by overlapping components.

18 Claims, 17 Drawing Sheets

Related U.S. Application Data

(60) Provisional application No. 62/742,852, filed on Oct. 8, 2018.

(51) Int. Cl.
    *A61F 2/00*         (2006.01)
    *A61F 2/848*      (2013.01)
    *A61F 2/95*       (2013.01)

(52) U.S. Cl.
    CPC ....... *A61F 2/848* (2013.01); *A61F 2002/8483* (2013.01); *A61F 2002/9511* (2013.01); *A61F 2002/9528* (2013.01); *A61F 2220/0008* (2013.01); *A61F 2220/0025* (2013.01); *A61F 2230/0069* (2013.01); *A61F 2230/0091* (2013.01); *A61F 2250/0059* (2013.01); *A61F 2250/0067* (2013.01)

(56) References Cited

U.S. PATENT DOCUMENTS

| | | | |
|---|---|---|---|
| 7,520,903 B2 | 4/2009 | Ferreyrol | |
| 7,753,945 B2 | 7/2010 | Bruun et al. | |
| 8,337,542 B2 | 12/2012 | Jantzen et al. | |
| 8,414,909 B2 | 4/2013 | Wang | |
| 8,623,066 B2 | 1/2014 | Looi et al. | |
| 8,690,822 B2 | 4/2014 | Papp | |
| 8,764,814 B2 | 7/2014 | Solem | |
| 8,771,340 B2 | 7/2014 | Densford | |
| 8,956,398 B2 | 2/2015 | George et al. | |
| 9,198,784 B2 | 12/2015 | Andreas et al. | |
| 9,220,618 B2 | 12/2015 | Igaki et al. | |
| 9,445,929 B2 | 9/2016 | Longo et al. | |
| 9,566,367 B2 | 2/2017 | Stekker et al. | |
| 9,597,206 B2 | 3/2017 | Seddon et al. | |
| 9,675,473 B2 | 6/2017 | Clerc et al. | |
| 9,724,220 B2 | 8/2017 | Rasmussen | |
| 9,770,575 B2 | 9/2017 | Wesselmann et al. | |
| 9,814,608 B2 | 11/2017 | Clerc et al. | |
| 9,855,160 B2 | 1/2018 | Armstrong et al. | |
| 10,004,615 B2 | 6/2018 | Sherry | |
| 10,039,659 B2 | 8/2018 | Bialas et al. | |
| 10,307,273 B2 | 6/2019 | Rubesch et al. | |
| 10,342,684 B2 | 7/2019 | Firstenberg et al. | |
| 10,668,188 B2 | 6/2020 | Wang | |
| 11,648,139 B2 * | 5/2023 | Jimenez, Jr. | A61F 2/966 623/1.11 |
| 2002/0087176 A1 | 7/2002 | Greenhalgh | |
| 2002/0156496 A1 | 10/2002 | Chermoni | |
| 2004/0181272 A1 | 9/2004 | Chambers | |
| 2005/0096731 A1 | 5/2005 | Looi et al. | |
| 2005/0288763 A1 * | 12/2005 | Andreas | A61F 2/97 623/1.11 |
| 2006/0115493 A1 | 6/2006 | Hone et al. | |
| 2008/0082154 A1 | 4/2008 | Tseng et al. | |
| 2008/0109065 A1 | 5/2008 | Bowe | |
| 2009/0254166 A1 * | 10/2009 | Chou | A61B 34/30 623/1.2 |
| 2010/0234935 A1 | 9/2010 | Bashiri | |
| 2011/0046709 A1 | 2/2011 | Coffey | |
| 2011/0054503 A1 | 3/2011 | Rizk et al. | |
| 2011/0077731 A1 | 3/2011 | Lee et al. | |
| 2012/0101560 A1 | 4/2012 | Kluck | |
| 2012/0203336 A1 | 8/2012 | Annest et al. | |
| 2017/0100266 A1 | 4/2017 | Fulkerson et al. | |
| 2017/0112513 A1 | 4/2017 | Marchand et al. | |
| 2017/0196717 A1 | 7/2017 | Fulkerson et al. | |
| 2018/0256376 A1 * | 9/2018 | Osbrink | A61F 2/958 |
| 2018/0303594 A1 | 10/2018 | Eller et al. | |
| 2018/0360589 A1 | 12/2018 | Nolan et al. | |
| 2019/0167456 A1 | 6/2019 | Collins et al. | |
| 2020/0139017 A1 | 5/2020 | Meyer-Kobbe et al. | |
| 2020/0171214 A1 | 6/2020 | Dietz | |
| 2020/0214825 A1 | 7/2020 | Gassler | |

FOREIGN PATENT DOCUMENTS

| | | |
|---|---|---|
| CN | 103491903 | 1/2014 |
| CN | 103860292 | 6/2014 |
| EP | 1506747 | 2/2005 |
| EP | 2414021 | 2/2012 |
| EP | 2531229 | 12/2012 |
| EP | 2545887 | 1/2013 |
| EP | 2550030 | 1/2013 |
| EP | 3290008 | 3/2018 |
| WO | WO 2008/018869 | 2/2008 |
| WO | WO 2018/213352 | 11/2018 |
| WO | WO 2020/101675 | 5/2020 |
| WO | WO 2020/172560 | 8/2020 |

OTHER PUBLICATIONS

Invitation to Pay Additional Fees from PCT/US2019/054847, dated Jan. 29, 2020, 13 pages.
Chinese Office Action from Chinese Patent Application No. 201980066102.4, dated Apr. 2, 2024, 18 pages including Machine-generated English language translation.
Japanese Office Action from Japanese Patent Application No. 2021-544101, dated Sep. 1, 2023, 7 pages including English language translation.
Australian Examination Report from Australian Patent Application No. 2019356771, dated May 27, 2024, 3 pages.
Chinese Office Action from Chinese Patent Application No. 201980066102.4, dated Aug. 5, 2024, 23 pages including English language translation.
Chinese Notification to Grant from Chinese Patent Application No. 201980066102.4, dated Jan. 2, 2025, 7 pages with English translation.

\* cited by examiner

DELIVERY SYSTEMS FOR STENTS HAVING PROTRUDING FEATURES

CROSS-REFERENCE TO RELATED APPLICATIONS

This application is a divisional of U.S. patent application Ser. No. 16/593,842, entitled "DELIVERY SYSTEMS FOR STENTS HAVING PROTRUDING FEATURES," filed Oct. 4, 2019, which claims the benefit of U.S. Provisional Application No. 62/742,852, entitled "DELIVERY SYSTEMS FOR STENTS HAVING PROTRUDING FEATURES," filed Oct. 8, 2018, the entirety of which is incorporated herein by reference.

TECHNICAL FIELD

The present description relates generally to delivery systems for expandable elements, such as stents or scaffolds having spikes, flails, or other protruding features for penetrating target tissue and/or delivering drugs within a human patient.

BACKGROUND

A variety of devices can be used to deliver drugs at desired treatment locations within a patient. For example, a stent, such as a drug-eluting stent (DES), can be positioned at the location of a stenosis (arterial narrowing) caused by arteriosclerosis. DESs generally include a drug containing polymer coated over a metal stent or scaffold, or a bioresorbable stent or scaffold composed of a drug-containing polymer. After a DES is delivered to a treatment location within a body lumen (e.g., vessel), it is expanded against a wall of the body lumen (e.g., a vessel wall) and the drug is released via direct contact with the wall. Direct delivery of the drug to the vessel wall enables significantly lower doses than those required via other delivery means (e.g., pills or injections).

Figure 1:
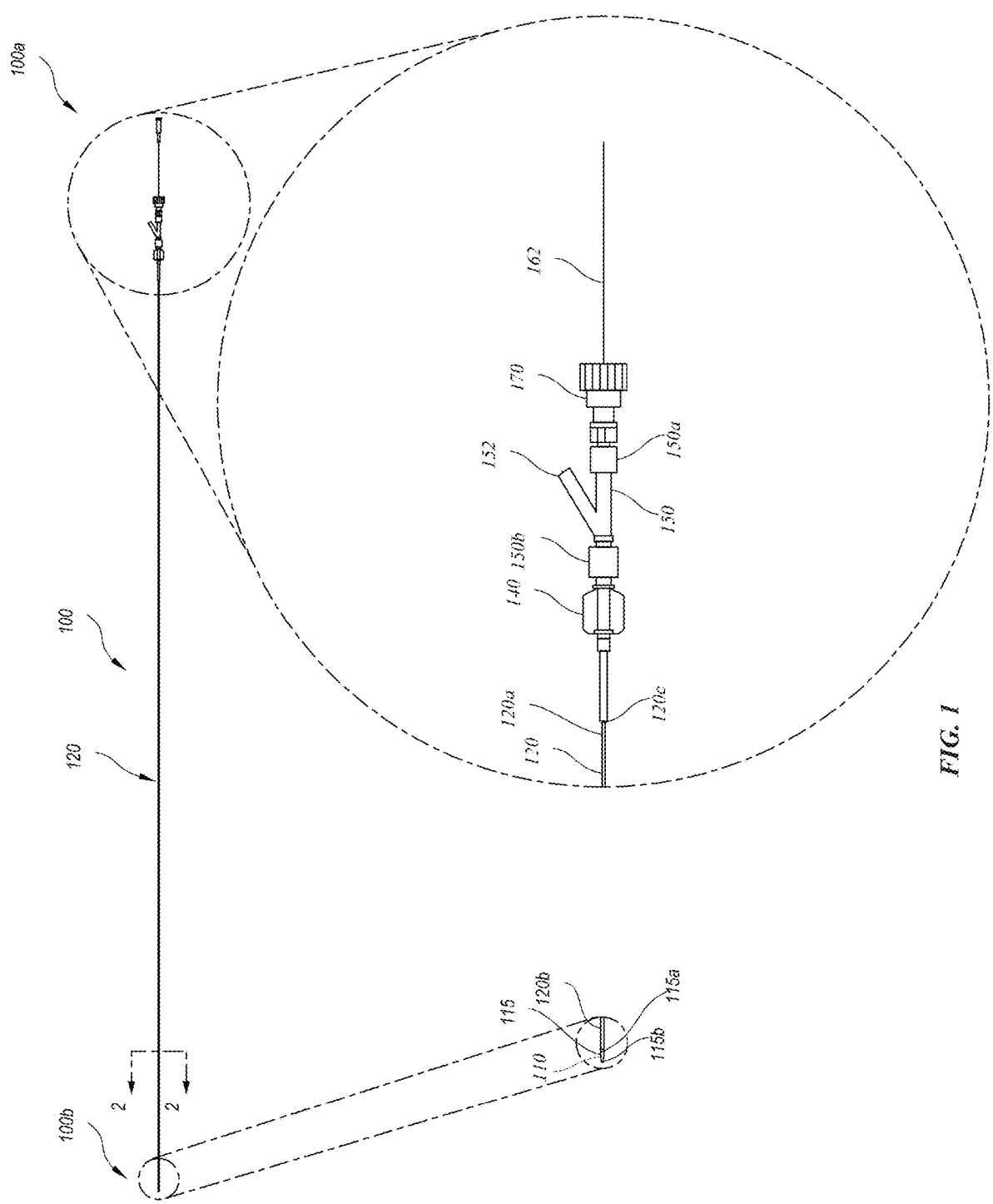
FIG. 1 shows a partially schematic side view of an example of a delivery system.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

The following disclosure describes various embodiments of delivery systems for expandable structures, such as stents or scaffolds, having spikes, flails, or other protruding features for penetrating target tissue and/or delivering drugs within a human patient, and associated devices and methods. The delivery systems can be configured to deliver and position expandable structures within a body lumen (e.g., vessel). In addition, these delivery systems can also be configured to deploy and expand the expandable structures in the body lumen. The delivery systems can further be configured to engage with the expanded structure and collapse the structure for removal from the body lumen. In some embodiments, the delivery systems can be configured to deliver another expandable structure or the same expandable structure to another body lumen, or the same body lumen, in a single procedure or during a plurality of procedures. Such delivery systems are expected to simplify and expedite transluminal procedures to more effectively deliver and position expandable structures within target tissues. The delivery systems can be used with more than one procedure, such as deployment of an expandable structure, when configured to recapture the deployed expandable structure.

In particular, delivery systems described herein can be provided with a stent that is positioned over an inflatable balloon for expansion and delivery of the stent to a target delivery location. By positioning the stent over and about the inflatable balloon, the stent is ready to be expanded by the balloon immediately upon unsheathing with respect to the outer shaft. Additionally or alternatively, a stent can be positioned in an axially offset arrangement with respect to a balloon to reduce the need for space required by overlapping components.

Certain details are set forth in the following description and FIGS. 1-32 to provide a thorough understanding of various embodiments of the disclosure. To avoid unnecessarily obscuring the description of the various embodiments of the disclosure, other details describing well-known structures and systems often associated with expandable structures, protruding features, and the components or devices associated with the manufacture of such structures are not set forth below. Moreover, many of the details and features shown in the figures are merely illustrative of particular embodiments of the disclosure. Accordingly, other embodiments can have other details and features without departing from the spirit and scope of the present disclosure. A person of ordinary skill in the relevant art will therefore understand that the present technology, which includes associated devices, systems, and procedures, may include other embodiments with additional elements or steps, and/or may include other embodiments without several of the features or steps shown and described below with reference to FIGS. 1-32. Furthermore, various embodiments of the disclosure can include structures other than those illustrated in the figures and are expressly not limited to the structures shown in the figures.

FIG. 1 shows a partially schematic side view of a delivery system 100 for a stent in a delivery state (e.g., low-profile or collapsed configuration). The delivery system 100 includes an outer shaft 120 (e.g., a catheter) having one or more lumens for containing an inner shaft 110 and/or a guidewire 162. In some embodiments, the outer shaft 120 may also include one or more layers. In these embodiments, for example, the layers of the outer shaft 120 can include an inner layer, an outer layer, a liner, or a combination thereof. Each of the layers can be formed from materials including a polymer, high-density polyethylene (HDPE), polytetrafluoroethylene, silicone, Pebax® (polyether block amide) or a combination thereof. In some embodiments, each of the layers of the outer shaft 120 are formed from the same material. In other embodiments, however, one or more of the layers may be formed from different materials.

The inner shaft 110 can extend from a connector 150, through the outer shaft 120, and beyond the distal portion 120*b* of the outer shaft 120. The inner shaft 110 can be formed as a tubular structure (with or without a slit), such as a coiled tube, a braided tube, a reinforced tube, or a combination thereof, and may be constructed of a polymer material, such as a polyimide. The delivery system 100 can include a guidewire within the inner shaft 110 and accessible at a proximal end of the delivery system 100.

In the detailed view of the distal portion 100*b* of the delivery system 100, a tip 115 (e.g., an atraumatic tip) is disposed on a distal terminal end of the inner shaft 110. As illustrated, the tip 115 is adjacent to a distal terminal end of the outer shaft 120. At least a portion of the tip 115 can have the same cross-sectional dimension as the outer shaft 120, or the tip 115 may have a different cross-sectional dimension. In some embodiments, a distal end 115*b* of the tip 115 is tapered such that the distal end 115*b* has a smaller cross-sectional dimension compared to a proximal end 115*a* of the tip. Distal and/or proximal edges of the tip 115 may be curved/rounded so as to prevent the tip 115 from getting caught (e.g., stuck) on other portions of the delivery system 100 during delivery, positioning, deployment, etc. The tip 115 can be formed of the same material(s) as the outer shaft 120. In other embodiments, however, the tip 115 can be formed from different material(s) than the outer shaft 120.

The inner shaft 110 and the outer shaft 120 can be sized and shaped for intravascularly accessing a target site (e.g., treatment site) of the patient. In some embodiments, for example, the outer shaft 110 has a length of about 150 cm to about 180 cm and a suitable cross-sectional dimension for positioning within a subject's vasculature. The length of the inner shaft 110 can be a working length, such as a length that can be positioned within a subject's vasculature. In some embodiments, for example, the working length is about 70 cm to about 300 cm, about 150 cm to about 250 cm, or about 70 cm, about 80 cm, about 90 cm, about 100 cm, about 110 cm, about 120 cm, about 130 cm, about 140 cm, about 150 cm, about 160 cm, about 170 cm, about 180 cm, about 190 cm, about 200 cm, about 210 cm, about 220 cm, about 230 cm, about 240 cm, about 250 cm, about 260 cm, about 270 cm, about 280 cm, about 290 cm, or about 300 cm. In other embodiments, the outer shaft 120 has a length of about 130 centimeters (cm) to about 140 cm and a cross-sectional dimension of about 4 French, about 5 French, or about 6 French. The length of the outer shaft 120 can be a working length, such as a length that can be positioned within a subject's vasculature. In some embodiments, the working length is about 50 cm to about 200 cm, about 100 cm to about 150 cm, or about 50 cm, about 60 cm, about 70 cm, about 80 cm, about 90 cm, about 100 cm, about 110 cm, about 120 cm, about 125 cm, about 130 cm, about 135 cm, about 140 cm, about 145 cm, about 150 cm, about 155 cm, about 160 cm, about 170 cm, about 180 cm, about 190 cm, or about 200 cm.

In the detailed view of the proximal portion 100*a* of the delivery system 100 in FIG. 1, a proximal end 120*c* of the outer shaft is coupled to an outer shaft hub 140. In the illustrated embodiment, the outer shaft hub 140 is coupled to the outer shaft 120 (e.g., via bonding). In other embodiments, however, the proximal end 120*c* of the outer shaft is directly coupled to the outer shaft hub 140.

The outer shaft hub 140 is further coupled to a connector 150 (e.g., y-connector) having a lumen extending therethrough (not shown). In particular, a distal end 150*b* of the connector 150 can be coupled to the outer shaft hub 140 via a mating feature and a receiving feature (not shown). The mating and receiving features can be coupled to the proximal portion of the outer shaft 120 or the distal end 150*b* of the connector 150. The connector 150 further includes a port 152 extending radially and/or longitudinally therefrom. The delivery system 100 can optionally include a hemostasis connector 170 coupled to a proximal end 150a of the y-connector 150. While the proximal end 120c is illustrated with particular components in a particular arrangement, it will be understood that additional or fewer components can be included in similar or other arrangements to meet the needs of the system.

The delivery system 100 is configured to carry a stent, discussed further herein, in a delivery/collapsed state within a distal portion of the outer shaft 120. The stent can be at least partially ensheathed by the outer shaft 120. In some embodiments, the stent can be fixedly or removably coupled to the inner shaft 110. Although the delivery system 100 is illustrated as a delivery system for stents, it will be appreciated that embodiments of the present technology can also include cages, meshes, balloons, membranes, tubular structures, circumferential bodies, expandable elements, expandable membranes, expandable structures, expandable tubular structures, and circumferentially expandable catheter tips with and without guidewire lumens.

Figure 2:
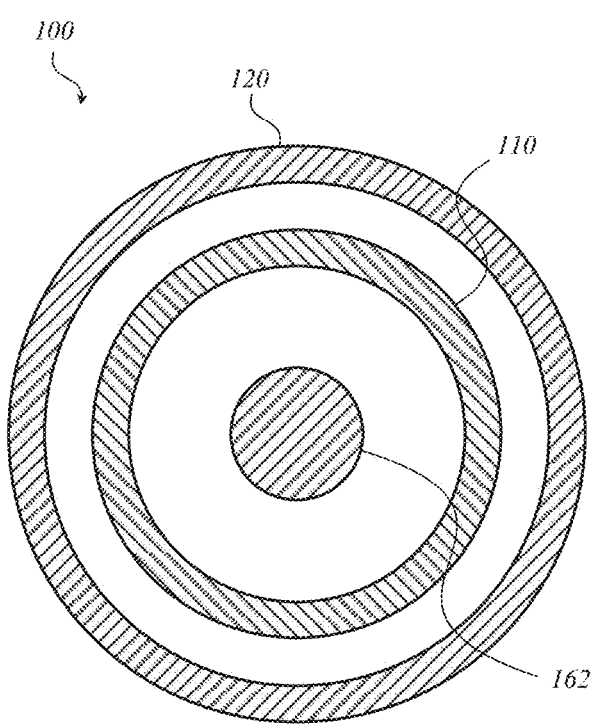
FIG. 2 shows a cross-sectional view of an example region of the delivery system of FIG. 1 taken along line 2-2.

FIG. 2 shows a cross-sectional view of a region of the delivery system 100 of FIG. 1 taken along line 2-2. As illustrated in FIG. 2, the inner shaft 110 can be at least partially disposed within a lumen of the outer shaft 120 and the guidewire 162 can be at least partially disposed within a lumen of the inner shaft 110. In some embodiments, the outer shaft 120, the inner shaft 110, and/or the guidewire 162 each have a circular cross-sectional shape. In other embodiments, however, the outer shaft 120, the inner shaft 110, and/or the guidewire 162 can have other cross-sectional shapes, such as an ovoid shape, a "C" shape, a rectangular shape, a triangular shape, or the like.

The guidewire 162 and the inner shaft 110 can be positioned within the lumen of the outer shaft 120 in any configuration, such as anteriorly and posteriorly as illustrated, or medially and laterally. Furthermore, the guidewire 162 and the inner shaft 110 can be positioned in the lumen of the outer shaft 120 with respect to one another as illustrated, or the guidewire 162 can be positioned outside the inner shaft 110. A fluid pathway can be defined within the lumen of the inner shaft 110, for example along the length of the guidewire 162. The fluid pathway can connect to and/or be accessible by the port 152 of the connector 150.

Figure 3:
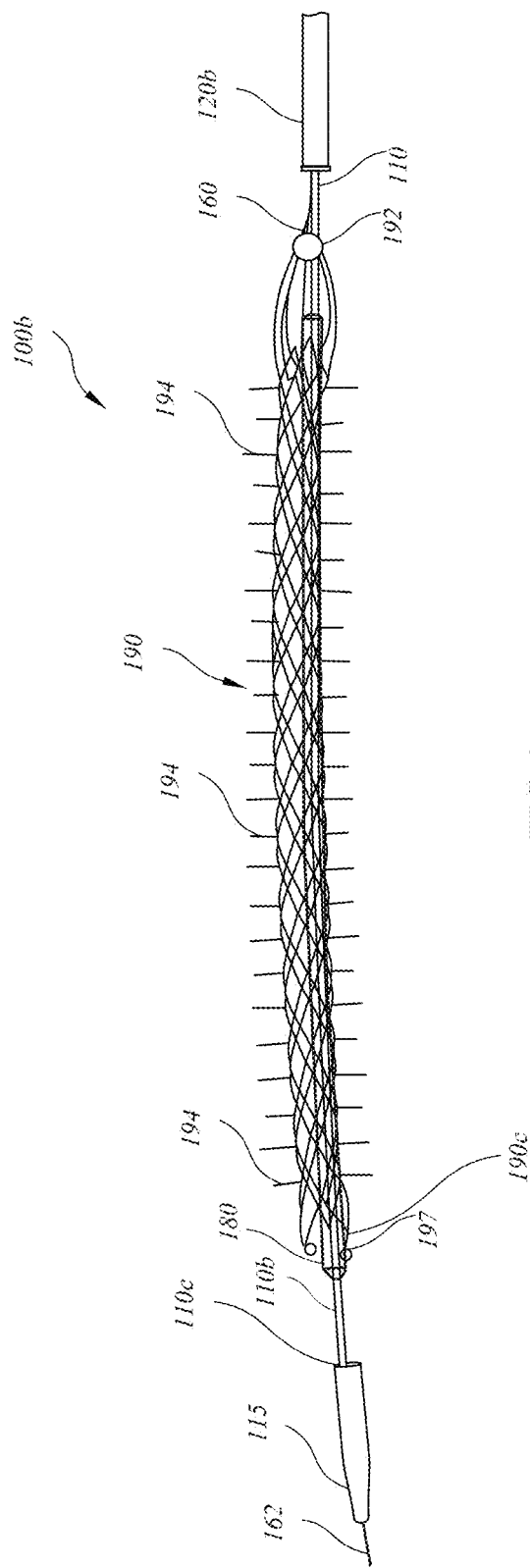
FIG. 3 shows an enlarged, partially schematic side view of a distal portion of the delivery system of FIG. 1 with an unconstrained stent.

FIG. 3 shows a side view of a distal portion 100b of the delivery system 100 of FIG. 1 in a deployed state. In the illustrated embodiment, a stent 190 extends over a balloon 180 and is coupled to the delivery catheter shaft and has been unsheathed from the distal portion 120b of the outer shaft. A proximal visualization marker 192 is disposed on the stabilizing wire 160 near a proximal portion of the stent 190 and distal visualization markers 197 are disposed on a distal end 190c of the stent. In some embodiments, the proximal visualization marker 192 and/or the distal visualization marker 197 may be disposed on the stabilizing wire 160. The visualization markers 192 and/or 197 can be formed from any material that can be visualized while the stent 190 is intravascularly positioned (e.g., within a target blood vessel). In one embodiment, for example, the visualization markers 192 and/or 197 are radiopaque markers. The stabilizing wire 160 can be connected to the inner shaft 110, such that movement of the inner shaft 110 correspondingly urges the stent 190 via the stabilizing wire 160, as discussed further herein. Alternatively, the stabilizing wire 160 can be independently movable relative to the inner shaft 110, as discussed further herein.

The tip 115 is disposed on a terminal end 110c of the inner shaft 110 and can surround the terminal end 110c extending proximally along the distal portion 110b and/or distally from the terminal end 110c. The inner shaft 110 extends distally from the distal portion 120b of the outer shaft 120, through a lumen of the stent 190, and, optionally, extends distally from the distal end of the stent 190. In the deployed configuration, protruding features 194 extend radially from a longitudinal axis of the stent 190, as discussed further herein.

The inner shaft 110 can also include an inflatable balloon (not shown), as discussed further herein. The inflatable balloon can be axially overlapping with the stent 190, distal to the stent 190, or proximal to the stent 190 while the stent 190 is in a delivery state (e.g., low-profile or collapsed configuration) within the outer shaft 120 and/or while the stent 190 is initially deployed from the delivery state.

The guidewire 162 can extend through the inner shaft 110 and beyond the tip 115. Accordingly, the guidewire 162 can be advanced ahead of other portions of the delivery system 100. The inner shaft 110, the stent 190, and the outer shaft 120 can be advanced over the guidewire 162 until the stent 190 is aligned with a desired target delivery location. The length of the guidewire 162 that overlaps other portions of the delivery system 100 can be within the inner shaft 110, so that it does not interfere with any other components of the delivery system 100.

Figure 4:
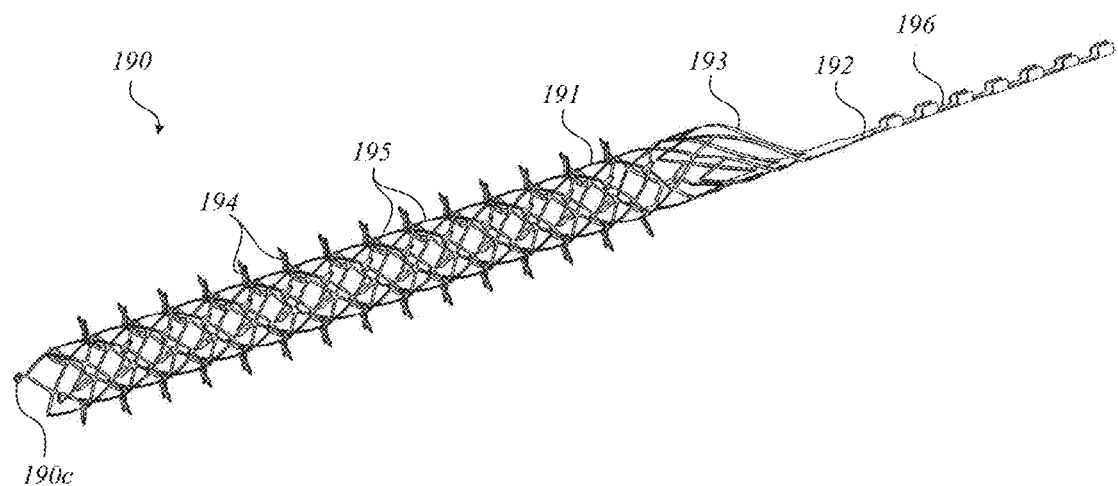
FIG. 4 shows a perspective view of an example of a stent.
Figure 5:
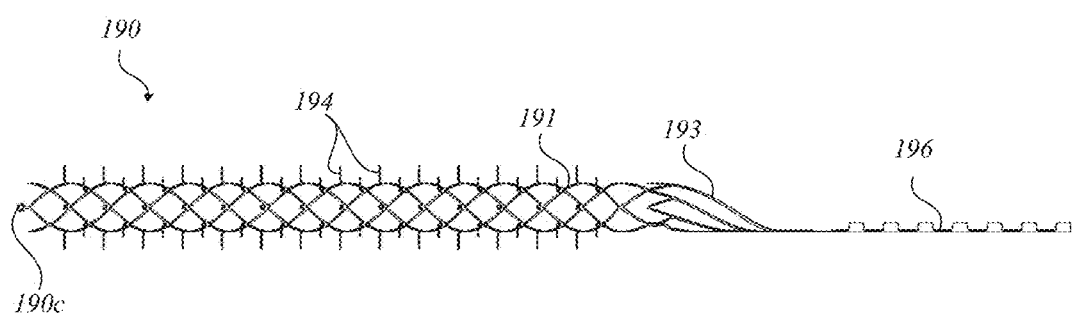
FIG. 5 shows a side view of the stent of FIG. 4.
Figure 6:
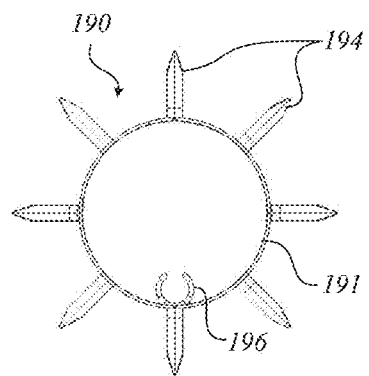
FIG. 6 shows a front view of the stent of FIG. 4.

As shown in FIGS. 4-6, the expandable stent 190 is provided with a frame 191 and multiple protruding features 194. The frame 191 and the protruding features 194 can be configured to radially expand after the stent 190 has been unsheathed from the outer shaft 120. The stent 190 can be self-expanding upon release from a constraint. Additionally or alternatively, the stent 190 can be expandable by radial forces applied from a balloon that is inflated while within the stent 190. The frame 191 can include multiple struts 195 arranged in a pattern that supports compression, expansion, flexibility, and bendability of the stent 190. The frame 191 can form a generally cylindrical shape along at least a portion of the stent 190. At least a portion of each protruding feature 194 can extend at least partially distally from the frame 191 (e.g., towards the distal end 190c). For example, at least a portion of each protruding feature 194 can extend parallel to a longitudinal axis of the stent 190. At least a portion (e.g., terminal end portion) of each protruding feature 194 can extend at least partially radially away from the frame 191. For example, at least a portion of each protruding feature 194 can extend radially outwardly (e.g., perpendicular to) the longitudinal axis of the stent 190. With at least a portion of each protruding feature 194 extending distally from the frame 191, the protruding features 194 can be readily retracted into the outer shaft 120 by folding down and extending distally when the outer shaft 120 is advanced from a proximal side of the stent 190 in a distal direction over the stent 190. The protruding features 194 can optionally include drugs for delivery to a target delivery location upon expansion of the stent 190. However, it will be understood that a stent 190 can omit drugs for delivery and treat a target delivery location by penetrating tissue with the protruding features 194.

The frame 191, struts 195, and/or protruding features 194 can be composed of or formed from a variety materials including, e.g., nitinol, cobalt chromium, stainless steel, any of a variety of other metals or metal alloys, or a combination thereof. The frame 191, struts 195, and/or protruding features 194 may also be composed of or formed from bioresorbable biodegradable, nanoporous or non-bioresorbable, non-biodegradable, non-nanopourous materials including, e.g., one or more polymers, nitinol, plastic materials, etc., or a combination thereof. In some embodiments, the frame 191 and the struts 195 can be formed from a bioresorbable material and the protruding features 194 can be formed from a non-bioresorbable material, such as nitinol. In these embodiments, the protruding features 194 can remain engaged with or penetrating a portion of the body lumen after the expanded frame 191 and struts 195 bio-resorb. After the expanded frame 191 and struts 195 bio-resorb, the body lumen where the stent 190 had been expanded is no longer partially occluded by the frame 191 and the struts 195 allowing for larger volumes of fluids, such as aqueous pharmaceutical compositions, to pass through the body lumen and contact the luminal wall. The protruding features 194 may also be formed of a bio-resorbable material and, once the stent 190 has bio-resorbed, the spaces in the body lumen wall vacated by the protruding features 194 can be contacted by the fluids passing through the body lumen. In this way, the stent 190 can increase a surface area of the body lumen wall contacted by the fluid.

The protruding features 194 may also be carried by more than one strut 195, the frame 191, or a combination thereof. The protruding features 194 may be integrally formed with the struts 195, for example by bending or twisting a portion of one or more struts and/or the frame 191 away from a longitudinal axis of the stent 190 or, alternatively, the protruding features 194 may be separate, discrete components that are attached to desired locations along the struts 195 and/or the frame 191.

The stent 190 can include an anchor portion 196 that securely connects to a component for controlling, positioning, and/or adjusting the stent 190. For example, the anchor portion 196 can securely connect the stent 190 to the inner shaft 110. Alternatively, the anchor portion 196 can securely connect the stent 190 to the stabilizing wire 160. The anchor portion 196 can be offset from a central axis of the stent 190. For example, the anchor portion 196 can be radially aligned with, adjacent to, or near a portion of the frame 191 of the stent 190. The frame 191 of the stent 190 can be connected to the anchor portion 196 by an intermediate portion 193. The intermediate portion 193 can include multiple struts that may have varying widths to aide in column strength for deploying and retraction that extend from different portions of the frame 191, for example connecting to different circumferential portions at an end of the frame 191. The struts of the intermediate portion 193 can extend to the same or different axial locations along the anchor portion 196. The arrangement of the struts of the intermediate portion 193 can maintain an open central space along the entire length of the stent 190.

Figure 7:
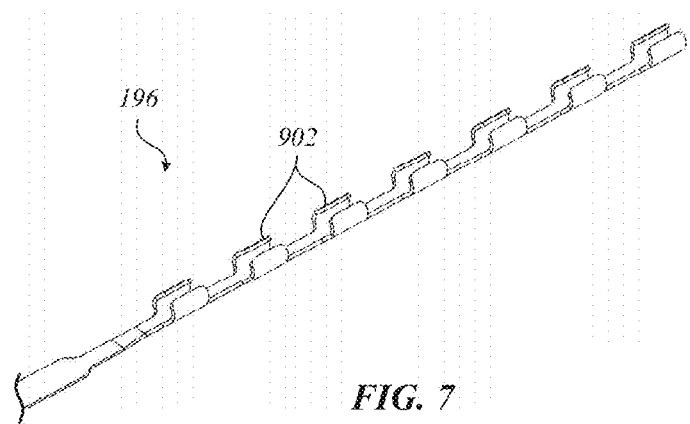
FIG. 7 shows a perspective view of an example of a connector end of the stent of FIG. 4.

As shown in FIGS. 7-10, the anchor portion 196 can be formed with one or more of a variety of arrangements. As shown in FIG. 7, the anchor portion 196 can include multiple ribs 902 extending circumferentially from different axial locations along the anchor portion 196. The ribs 902 can be positioned at different axial locations to provide multiple points of contact with a positioner, such as the inner shaft 110 and/or the stabilizing wire 160.

Figure 8:
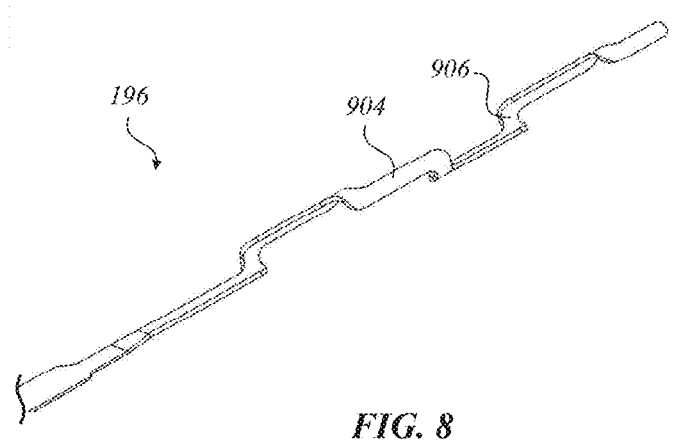
FIG. 8 shows a perspective view of another example of a connector end of the stent of FIG. 4.

As shown in FIG. 8, the anchor portion 196 can include different portions that extend in different directions. For example, the anchor portion 196 can include longitudinal portions 904 and circumferential portions 906. Axially adjacent pairs of the longitudinal portions 904 can be connected together by a corresponding circumferential portion 906. Likewise, axially adjacent pairs of the circumferential portions 906 can be connected together by a corresponding longitudinal portion 904. Different longitudinal portions 904 can have different circumferential positions to surround a coupled positioned at different circumferential positions thereon.

Figure 9:
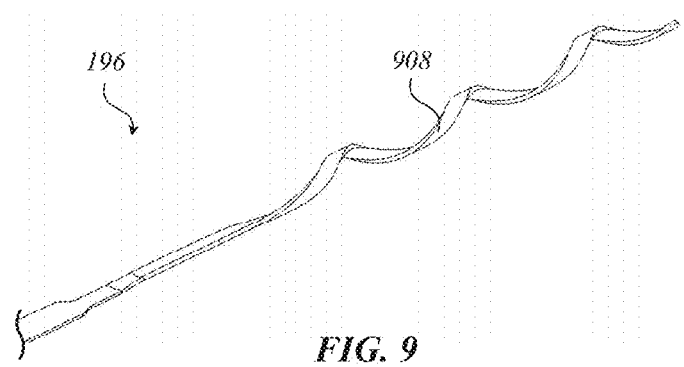
FIG. 9 shows a perspective view of another example of a connector end of the stent of FIG. 4.

As shown in FIG. 9, the anchor portion 196 can include a helical winding 908. For example, the anchor portion 196 can wind helically about a central space configured to receive the positioner therein. The helical winding 908 can include multiple (e.g., 2, 3, 4, 5, 6, 7, 8, or more than 8) turns. The helical winding 908 can include, in cross-section, a shape that provides a flat inner side for engaging the positioner while maintaining a low profile.

Figure 10:
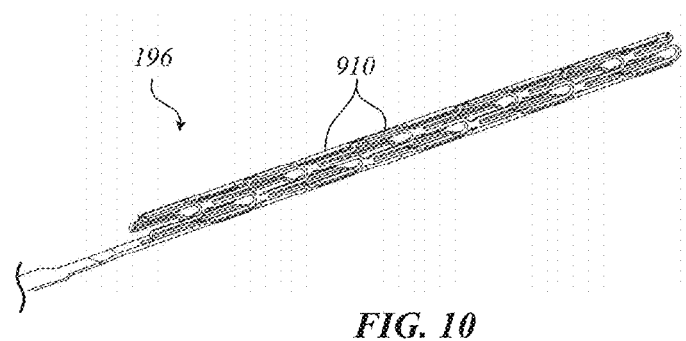
FIG. 10 shows a perspective view of another example of a connector end of the stent of FIG. 4.

As shown in FIG. 10, the anchor portion 196 can include an arrangement of multiple struts 910. The struts 910 can define a generally cylindrical shape for receiving and coupling to a positioner. The struts 910 can extend longitudinally and/or circumferentially about the space for receiving the positioner. The struts 910 can form any number of cells, which can vary in length and/or width relative to each other.

The anchor portion 196 can securely connect the stent 190 to a positioner, such as the inner shaft 110 and/or the stabilizing wire 160. For example, the anchor portion 196 can be pressed onto the positioner. By further example, the anchor portion 196 can be bonded to the positioner. Additionally or alternatively, a sleeve can be provided about at least a portion of the anchor portion 196 and/or the positioner. For example, a tube, such as shrink tubing molded from one or more flexible materials, including polyurethane and Pebex® (e.g., Pebex® 35D), can be provided as a sleeve over the anchor portion 196 and/or the positioner. Additionally or alternatively, the stabilizing wire 160 can be connected to the inner shaft 110 by one or more of a variety of methods, including laser welding, bonding, crimping, swaging, reflowing, etc. Additionally or alternatively, the anchor portion 196 can removably or reversibly connect the stent 190 to a positioner. For example, the anchor portion 196 can be provided with one or more detachment mechanisms (e.g., electrolytic, mechanical, or chemical) for controllably separating the stent 190 from the positioner. As such, the stent 190 can be controllably detached and left at a target delivery location.

Methods described herein provide delivery of the stent 190 to a target delivery location by operation of the delivery system 100. While methods in their various stages are discussed and illustrated herein, it will be understood that multiple variations of each method are also contemplated. For example, the methods can be performed in various orders of operations, with additional operations, or with fewer operations.

As shown in FIGS. 11-14, a delivery system 100 can be provided with a stent 190 that is positioned over an inflatable balloon 180 for expansion and delivery of the stent 190 to a target delivery location. By positioning the stent 190 over and about the inflatable balloon 180, the stent 190 is ready to be expanded by the balloon 180 immediately upon unsheathing with respect to the outer shaft 120.

Figure 11:
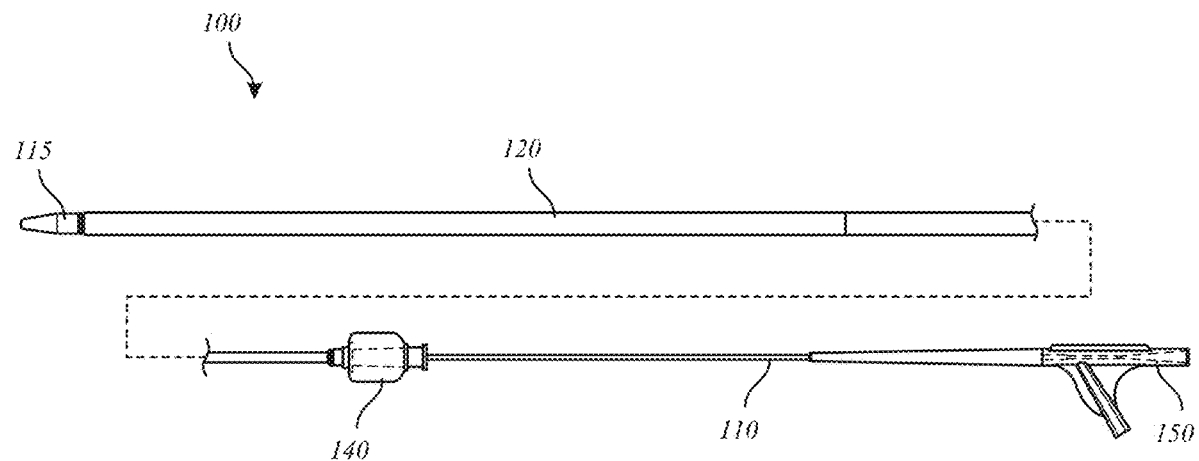
FIG. 11 shows a side view of an example of a delivery system in a first stage of deployment.

As shown in FIG. 11, the delivery system 100 is provided with the outer shaft 120 covering or ensheathing other components of the delivery system 100. For example, the outer shaft 120 can extend to the tip 115 positioned at a distal end of the inner shaft 110. The inner shaft 110 can extend within the outer shaft 120, with a length thereof accessible proximal to a proximal end of the outer shaft 120 (e.g., at the outer shaft hub 140). Additionally or alternatively, the connector 150 can be accessible proximal to a proximal end of the outer shaft 120 (e.g., at the outer shaft hub 140). As discussed above, a guidewire can be advanced ahead of the tip 115 (e.g., through the inner shaft 110) to provide a pathway for advancement of other components of the delivery system 100.

Figure 12:
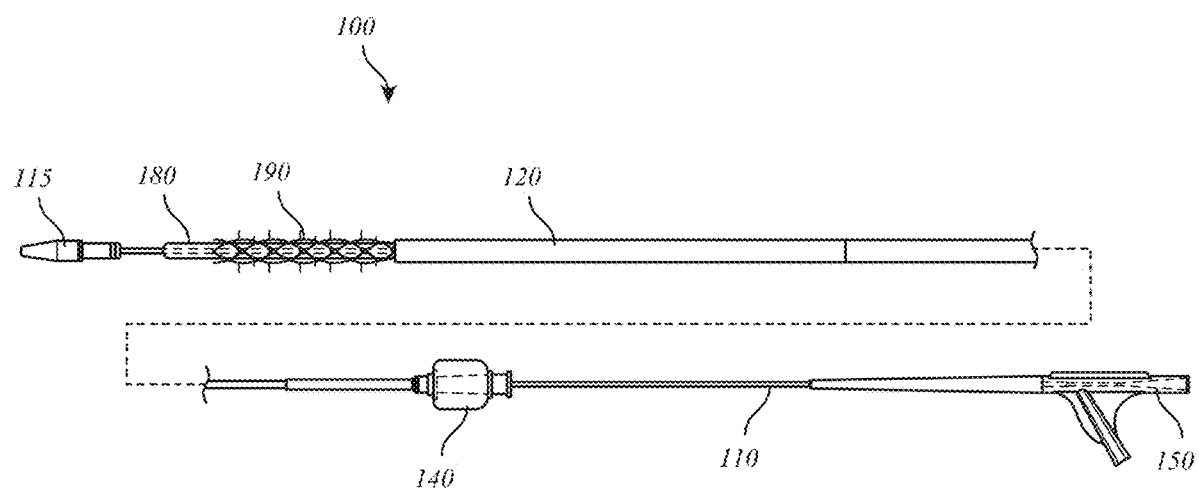
FIG. 12 shows a side view of the delivery system of FIG. 11 in a second stage of deployment.
Figure 13:
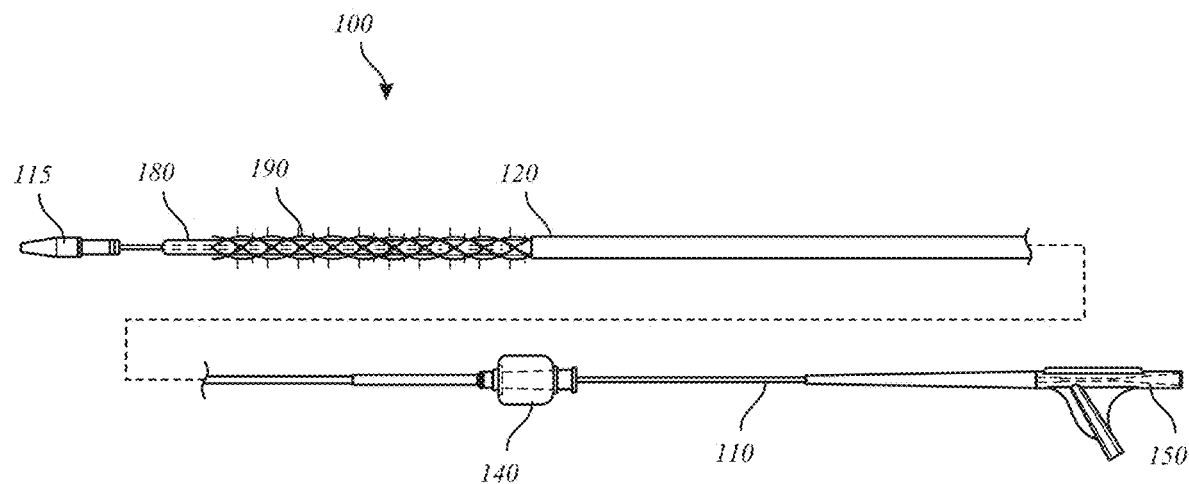
FIG. 13 shows a side view of the delivery system of FIG. 11 in a third stage of deployment.

As shown in FIGS. 12 and 13, the outer shaft 120 can be moved to unsheath the stent 190 and other components of the delivery system 100. For example, once the distal region of the delivery system 100 is positioned at a desired location, the outer shaft 120 is configured to be at least partially proximally retracted relative to the inner shaft 110 by retracting the outer shaft hub 140 relative to the connector 150. Once the outer shaft 120 is partially retracted, at least a portion of the stent 190 and/or the balloon 180 is unsheathed and protruding features 194 of the stent 190 are configured to radially expand outwardly away from the inner shaft 110.

As used herein, movement of various components can be relative to other components of the delivery system 100 and/or relative to a position apart from the delivery system 100 (e.g., a position within the anatomy of the patient, target delivery location, and/or tissue). The directions "proximal" and "distal" can be with respect to the delivery system 100, a component thereof, and/or a position apart from the delivery system 100. For example, movement of the guidewire 162 can be relative to the outer shaft 120, the inner shaft 110, the stent 190, and/or the balloon 180. It will be understood that while the guidewire 162 moves, the outer shaft 120, the inner shaft 110, the stent 190, and/or the balloon 180 can be stationary, moving in the same direction (e.g., at a different speed), or moving in a different (e.g., opposite) direction. It will be further understood that while the outer shaft 120, the inner shaft 110, the stent 190, and/or the balloon 180 moves, the guidewire 162 can be stationary, moving in the same direction (e.g., at a different speed), or moving in a different (e.g., opposite) direction. By further example, movement of the outer shaft 120 can be relative to the inner shaft 110, the stent 190, and/or the balloon 180. It will be understood that while the outer shaft 120 moves, the inner shaft 110, the stent 190, and/or the balloon 180 can be stationary, moving in the same direction (e.g., at a different speed), or moving in a different (e.g., opposite) direction. By further example, movement of the inner shaft 110, the stent 190, and/or the balloon 180 can be relative to outer shaft 120. It will be understood that while the inner shaft 110, the stent 190, and/or the balloon 180 move, the outer shaft 120 can be stationary, moving in the same direction (e.g., at a different speed), or moving in a different (e.g., opposite) direction.

Figure 14:
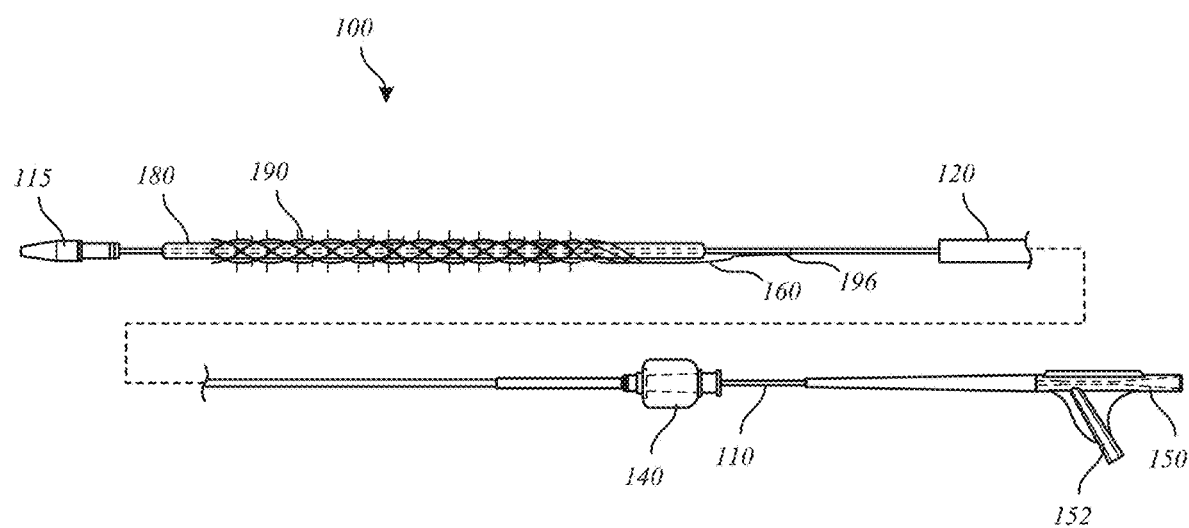
FIG. 14 shows a side view of the delivery system of FIG. 11 in a fourth stage of deployment.

As shown in FIG. 14, the outer shaft 120 has been retracted and the stent 190 is unsheathed. The stabilizing wire 160, connected to the inner shaft 110 by the anchor portion 196, is configured to engage with the proximal end of the stent 190 and control the position of the stent 190 during and after retraction of the outer shaft 120. Accordingly, the position of the stent 190 is maintained with respect to the inner shaft 110, including the balloon 180. For example, while some adjustment of the length and/or axial position of the stent 190 may occur during radial expansion of the stent 190, it will be understood that the stabilizing wire 160 can maintain the position of at least a portion of the stent 190 to be around and axially aligned with at least a portion of the balloon 180. The balloon 180 can have an axial length that is greater than the axial length of the stent 190, so that an entirety of the stent 190 is overlapping with the balloon 180. As shown in FIG. 14, the stabilizing wire 160 can connect the stent 190 to a portion of the inner shaft 110 that is proximal to the balloon 180. Additionally or alternatively, the stabilizing wire 160 can connect the stent 190 to a portion of the inner shaft 110 that is distal to the balloon 180.

When both the stent 190 and the balloon 180 are unsheathed by the outer shaft 120 and exposed, the balloon 180 can be inflated to expand or further expand the stent 190. For example, an interior region of the balloon can be fluidly connected, via the inner shaft 110, to the port 152 of the connector 150. By providing a fluid through the port 152, the balloon 180 can be expanded, thereby expanding or further expanding the stent 190. The expansion with respect to target anatomy will be further discussed herein.

Following one or more of the above-described operations, the balloon 180 can be deflated. The stent 190 can be maintained for any duration of time in an expanded state. For example, the stent 190 can be maintained for a duration of time effective to provide therapeutic treatment (e.g., remodeling and/or drug delivery) to target anatomy and allows fluid flow through the expanded stent and deflated balloon where there is no fluid blockage through the treated site.

Additionally or alternatively, the delivery system 100 can be deployed at multiple locations. The stent 190 can be collapsed by moving the outer shaft 120 over the stent 190. The stent 190 and the balloon 180 can be moved to another target location, and one or more of the above-described operations can be repeated.

Additionally or alternatively, the delivery system 100 can be removed. The stent 190 can be collapsed by moving the outer shaft 120 over the stent 190. Components of the delivery system 100 can be removed from the patient by retracting proximally over the guidewire.

Additionally or alternatively, the stent 190 can be detached from the inner shaft 110 and left as an implant within the patient. Following detachment, other components of the delivery system 100 can be removed from the patient by retracting proximally over the guidewire.

While the delivery system 100 is shown with a stent 190 positioned over a balloon 180 in a delivery state, it will be understood that other arrangements are contemplated. For example, a stent can be positioned in an axially offset arrangement with respect to a balloon to reduce the need for space required by overlapping components. Reference is made to a delivery system 200, as shown in FIGS. 16-20, a delivery system 300, as shown in FIGS. 21-24, and a delivery system 500, as shown in FIGS. 25-28. While each of the delivery system 200 and the delivery system 300 is in some aspects different than the delivery system 100, it will be understood that components and features of the delivery system 100 as described herein can apply to either or both of the delivery system 200 and the delivery system 300. Similar or like items can perform the same function as those shown in the delivery system 100, and the features of such items are not all discussed hereafter, for brevity.

Figure 15:
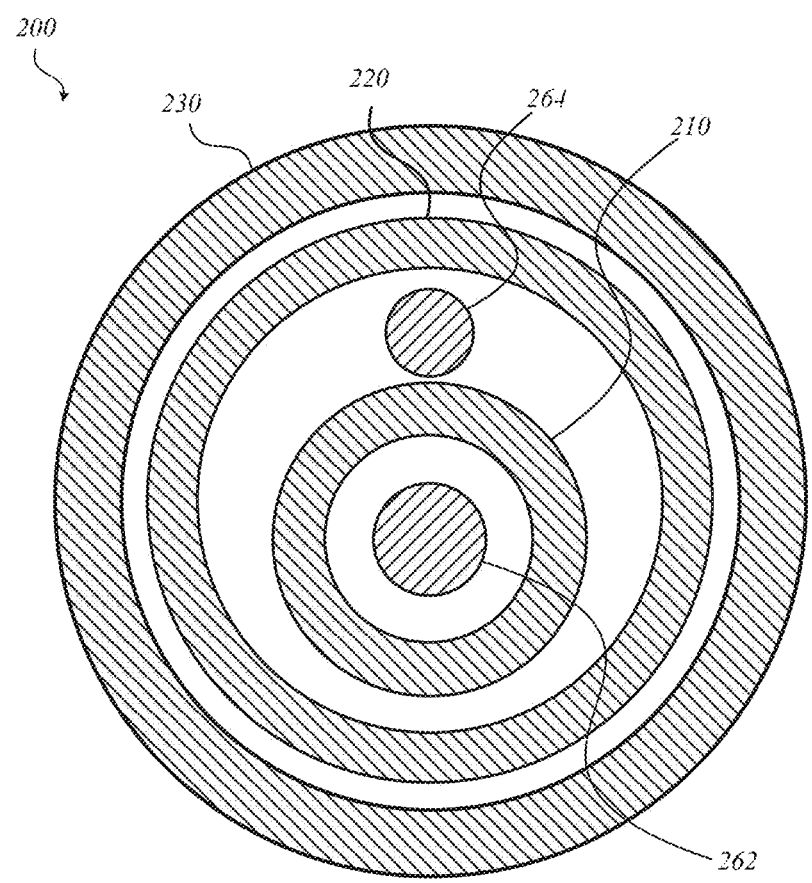
FIG. 15 shows a cross-sectional view of an example region of a delivery system.

Referring now to FIG. 15, with further reference to FIG. 1, a cross-sectional view of a region of a delivery system 200 is shown, wherein the delivery system 200 is similar in at least some aspects to the delivery system 100 shown in FIG. 1. For example, the sectional view of FIG. 15 can be taken along a line that positioned similarly as the line 2-2 in FIG. 1. As illustrated in FIG. 15, an inner shaft 210 can be at least partially disposed within a lumen of an outer shaft 220. Additionally, a stiffening wire 264 is provided between the outer shaft 220 and the inner shaft 210. The stiffening wire 264 can be of stainless steel or another material and can influence the luminal space and shaft stiffness and/or flexibility without modifying the material thickness of the shaft.

A guidewire 262 can be at least partially disposed within a lumen of the inner shaft 210. A lumen defined between the outer shaft 220 and the inner shaft 210 or within the inner shaft 210 can provide fluid communication to a balloon for inflation and deflation of the balloon. In some embodiments, the outer shaft 220, the inner shaft 210, the guidewire 262, and/or stiffening wire 264 each have a circular cross-sectional shape and a single lumen. In other embodiments, however, the outer shaft 220, the inner shaft 210, the guidewire 262, and/or stiffening wire 264 can have other cross-sectional shapes, such as an ovoid shape, a "C" shape, a rectangular shape, a triangular shape, or the like, with multiple lumens. For example, the stiffening wire 264 can have a shape that fits within the space between the outer shaft 220 and the inner shaft 210. For example, the cross-sectional shape of the stiffening wire 264 can be polygonal (e.g., rectangular) or crescent-shaped. The inner surface of the outer shaft 220 and/or the outer surface of the inner shaft 210 can have cross-sectional shapes that accommodate and/or guide the stiffening wire 264. A support shaft 230 can also be placed circumferentially around the inner shaft 210 or outer shaft 220 to increase column strength and stiffness of the catheter region. In some embodiments, the support shaft 230 can have a larger inner diameter and be attached to the outer shaft 220 to extend the overall catheter length and accommodate a larger proximal segment of the inner catheter 210 or stiffening wire 264. The support shaft placement can vary from the entire length of the inner shaft 210 to specific 10 cm, 20 cm, 30 cm, 40 cm segments of the inner shaft with varying gaps of 10 cm, 20 cm, 30 cm, 40 cm length to increase overall catheter stiffness. Attachment mechanisms may include bonding, reflowing, braiding, coiling, laser welding, etc. The support shaft 230 can also be made of high durometer plastics such as nylon, Pebax®, stainless steel, Nitinol, polyether ether ketone (PEEK), etc.

A stabilizing wire 260 can be coupled to a stent. The stabilizing wire 260 is slideably disposed within the outer shaft 220 and is sized and shaped to extend distally from the proximal end of the outer shaft and to extend proximally from a proximal end of a port. The stabilizing wire 260 can be formed of plastic, such as high durometer plastic including nylon, polyether ether ketone (PEEK), a metal, a metal alloy, such as nitinol, and/or combinations thereof. The stabilizing wire 260 can be configured to position the stent (not shown) at the desired treatment location and to at least generally maintain the position of the stent while the outer shaft 220 is withdrawn as described in greater detail below.

The stabilizing wire 260 can be sized and shaped to extend proximally from the proximal end of the port when the stent is positioned at the target site. For example, the stabilizing wire 260 can have a length of about 150 cm to about 180 cm and a suitable cross-sectional dimension for positioning within the patient's body lumen. The stabilizing wire 260 can have a working length (i.e., a length that can be positioned within the target body lumen) of about 70 cm to about 300 cm, about 150 cm to about 250 cm, or about 70 cm, about 80 cm, about 90 cm, about 100 cm, about 110 cm, about 120 cm, about 130 cm, about 140 cm, about 150 cm, about 160 cm, about 170 cm, about 180 cm, about 190 cm, about 200 cm, about 210 cm, about 220 cm, about 230 cm, about 240 cm, about 250 cm, about 260 cm, about 270 cm, about 280 cm, about 290 cm, or about 300 cm.

As shown in FIGS. 16-20, the delivery system 200 can be provided with a stent 290 that is positioned proximal to an inflatable balloon 280 for expansion and delivery of the stent 290 to a target delivery location. By positioning the stent 290 proximal to the inflatable balloon 280, the stent 290 and the balloon 280 are not overlapping (e.g., are axially offset) while in a delivery state within the outer shaft 220, and thereby reduce the space requirements within the outer shaft 220.

Figure 16:
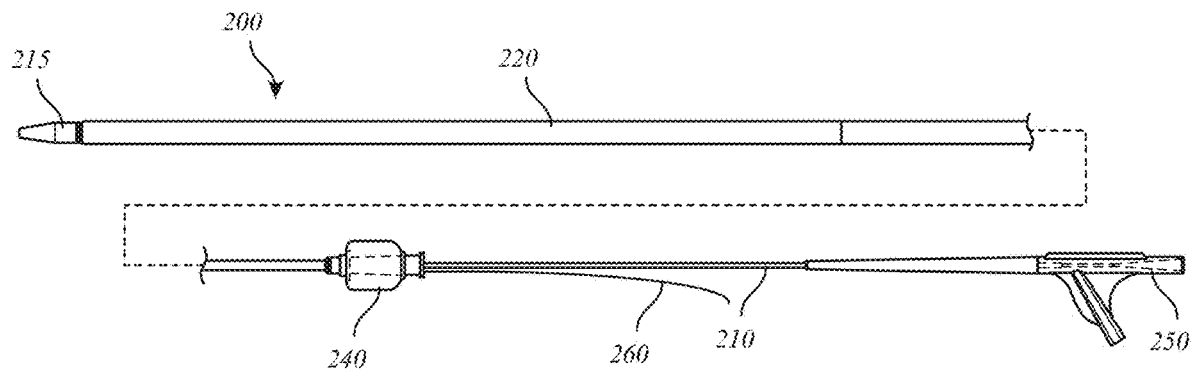
FIG. 16 shows a side view of another example of a delivery system in a first stage of deployment.

As shown in FIG. 16, the delivery system 200 is provided with the outer shaft 220 covering or ensheathing other components of the delivery system 200. For example, the outer shaft 220 can extend to a tip 215 positioned at a distal end of the inner shaft 210. The inner shaft 210 can extend within the outer shaft 220, with a length thereof accessible proximal to a proximal end of the outer shaft 220 (e.g., at the outer shaft hub 240). Additionally or alternatively, the connector 250 can be accessible proximal to a proximal end of the outer shaft 220 (e.g., at the outer shaft hub 240). A stabilizing wire 260 is also accessible proximal to a proximal end of the outer shaft 220 (e.g., at the outer shaft hub 240). A guidewire can be advanced ahead of the tip 215 (e.g., through the inner shaft 210) to provide a pathway for advancement of other components of the delivery system 200.

Figure 17:
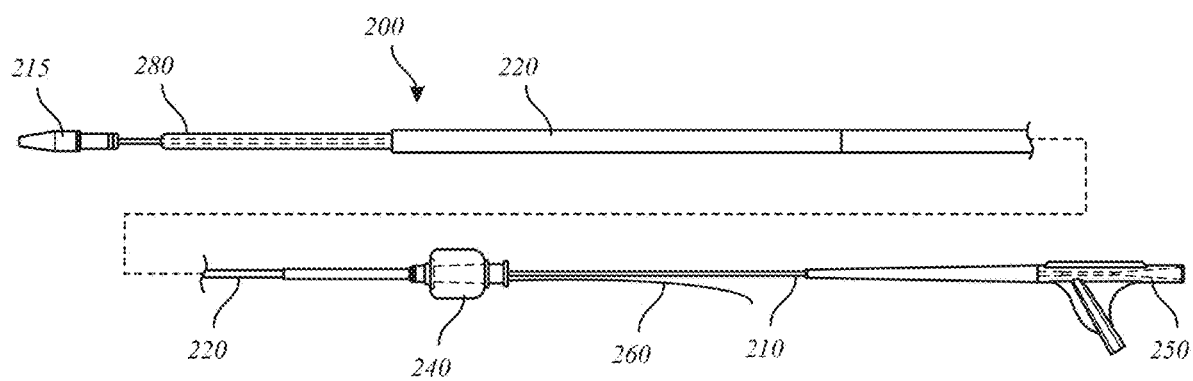
FIG. 17 shows a side view of the delivery system of FIG. 16 in a second stage of deployment.

As shown in FIG. 17, the outer shaft 220 can be moved to unsheath an inflatable balloon 280. For example, once the distal region of the delivery system 200 is positioned at a desired location, the outer shaft 220 is configured to be at least partially proximally retracted relative to the inner shaft 210 by retracting the outer shaft hub 240 relative to the connector 250. Once the outer shaft 220 is partially retracted, at least a portion of the balloon 280 is unsheathed.

Figure 18:
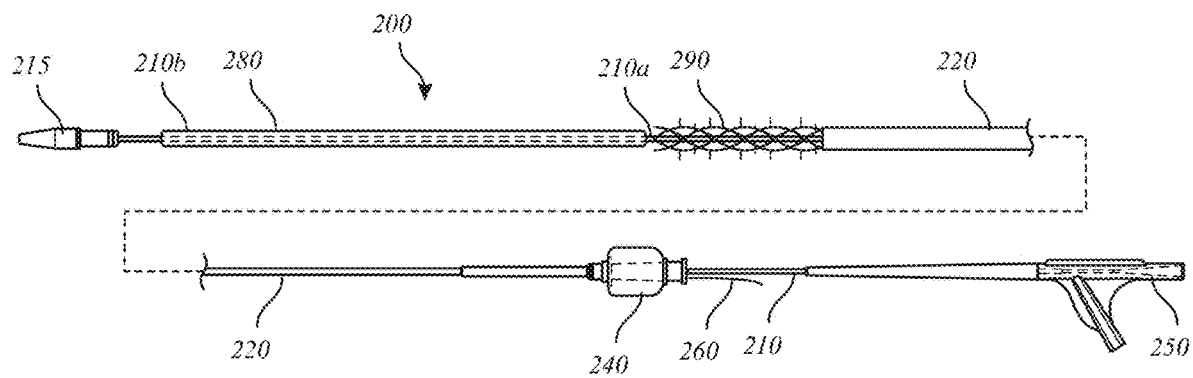
FIG. 18 shows a side view of the delivery system of FIG. 16 in a third stage of deployment.

As shown in FIG. 18, the outer shaft 220 can be further moved to unsheath a stent 290. Once the outer shaft 220 is further retracted, a portion of the stent 290 is unsheathed and protruding features 294 of the stent 290 are configured to radially expand outwardly away from the inner shaft 210. As shown, the balloon 280 is positioned at a distal portion 210b of the inner shaft 210, and the stent 290 is positioned at a proximal portion 210a of the inner shaft 210. The proximal portion 210a of the inner shaft 210 can have an outer cross-sectional dimension that is smaller than an outer cross-sectional dimension of the balloon 280, thereby permitting the stent 290 to be collapsed onto the proximal portion 210a in a smaller profile than would be achieved if the stent 290 were collapsed onto the balloon 280.

Figure 19:
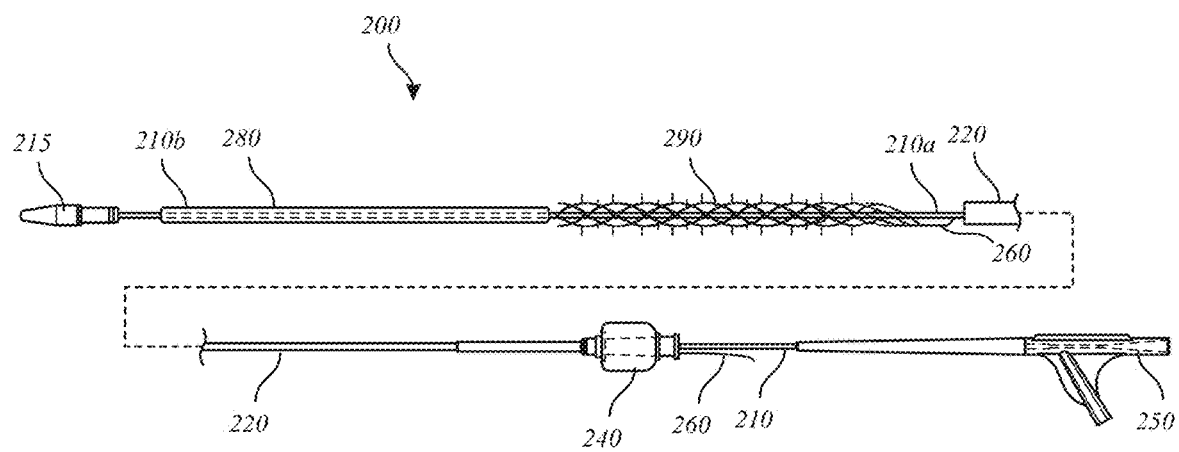
FIG. 19 shows a side view of the delivery system of FIG. 16 in a fourth stage of deployment.

As shown in FIG. 19, the outer shaft 220 has been retracted and the stent 290 is unsheathed. The stabilizing wire 260, accessible by a user, is configured engage with the proximal end of the stent 290 and control the position of the stent 290 during and after retraction of the outer shaft 220. The user can secure the stabilizing wire 260 relative to the inner shaft 210 while the outer shaft 220 is retracted so that the position of the stent 290 can be maintained with respect to the inner shaft 210, including the balloon 280, during retraction of the outer shaft 220.

Figure 20:
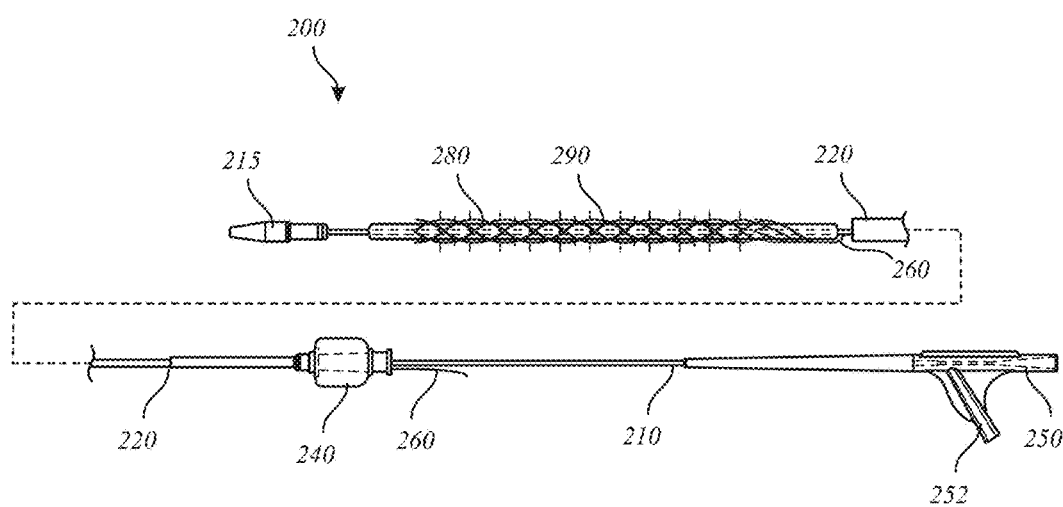
FIG. 20 shows a side view of the delivery system of FIG. 16 in a fifth stage of deployment.

As shown in FIG. 20, when both the stent 290 and the balloon 280 are unsheathed by the outer shaft 220 and exposed, the stent 290 can be axially aligned with the balloon 280. Because the inner shaft 210 extends through the stent 290, proximal retraction of the inner shaft 210 relative to the stent 290 can achieve axially alignment of the balloon 280 with the stent 290. The balloon 280 can have an axial length that is greater than the axial length of the stent 290, so that an entirety of the stent 290 is overlapping with the balloon 280 when axially aligned. Additionally or alternatively, the inner shaft 210 and the outer shaft 220 can be retracted together with respect to the stent 290.

The balloon 280 can be inflated to expand or further expand the stent 290. For example, an interior region of the balloon can be fluidly connected, via the inner shaft 210, to the port 252 of the connector 250. By providing a fluid through the port 252, the balloon 280 can be expanded, thereby expanding or further expanding the stent 290. The expansion with respect to target anatomy will be further discussed herein.

Following one or more of the above-described operations, the balloon 280 can be deflated. The stent 290 can be maintained for any duration of time in an expanded state. For example, the stent 290 can be maintained for a duration of time effective to provide therapeutic treatment (e.g., remodeling and/or drug delivery) to target anatomy.

Additionally or alternatively, the delivery system 200 can be deployed at multiple locations. The stent 290 can be collapsed by moving the outer shaft 220 over the stent 290. Optionally, the stent 290 can be axially realigned with the proximal portion 210a of the inner shaft 210 prior to collapse by the outer shaft 220. The stent 290 and the balloon 280 can be moved to another target location, and one or more of the above-described operations can be repeated.

Additionally or alternatively, the delivery system 200 can be removed. The stent 290 can be collapsed by moving the outer shaft 220 over the stent 290. Optionally, the stent 290 can be axially realigned with the proximal portion 210a of the inner shaft 210 prior to collapse by the outer shaft 220. Components of the delivery system 200 can be removed from the patient by retracting proximally over the guidewire.

Additionally or alternatively, the stent 290 can be detached from the stabilizing wire 260 and left as an implant within the patient. Following detachment, other components of the delivery system 200 can be removed from the patient by retracting proximally over the guidewire.

As shown in FIGS. 21-24, the delivery system 300 can be provided with a stent 390 that is positioned distal to an inflatable balloon 380 for expansion and delivery of the stent 390 to a target delivery location. By positioning the stent 390 distal to the inflatable balloon 380, the stent 390 and the balloon 380 are not overlapping (e.g., are axially offset) while in a delivery state within the outer shaft 320, and thereby reduce the space requirements within the outer shaft 320.

Figure 21:
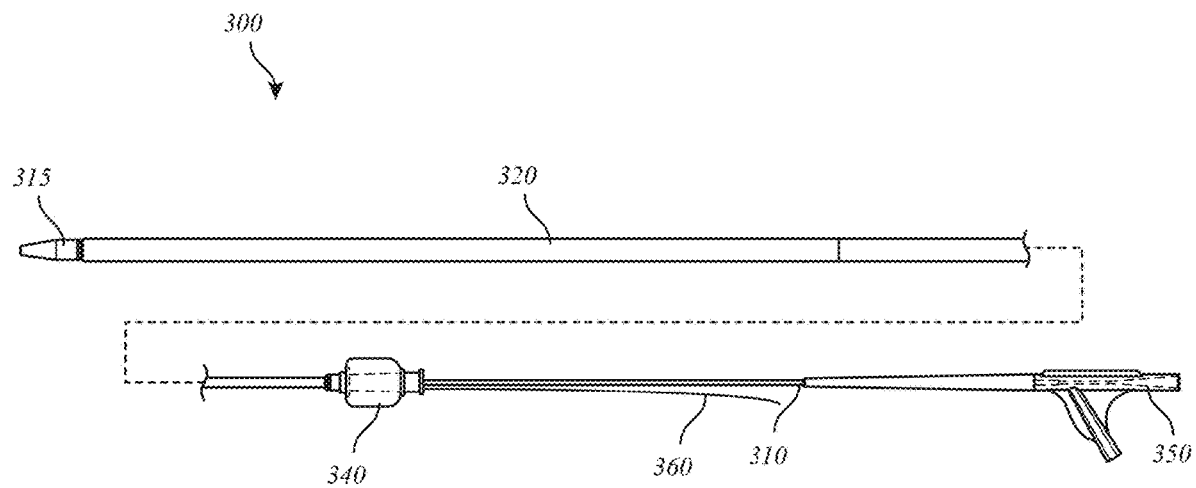
FIG. 21 shows a side view of another example of a delivery system in a first stage of deployment.

As shown in FIG. 21, the delivery system 300 is provided with the outer shaft 320 covering or ensheathing other components of the delivery system 300. For example, the outer shaft 320 can extend to a tip 315 positioned at a distal end of the inner shaft 310. The inner shaft 310 can extend within the outer shaft 320, with a length thereof accessible proximal to a proximal end of the outer shaft 320 (e.g., at the outer shaft hub 340). Additionally or alternatively, the connector 350 can be accessible proximal to a proximal end of the outer shaft 320 (e.g., at the outer shaft hub 340). A stabilizing wire 360 is also accessible proximal to a proximal end of the outer shaft 320 (e.g., at the outer shaft hub 340). A guidewire can be advanced ahead of the tip 315 (e.g., through the inner shaft 310) to provide a pathway for advancement of other components of the delivery system 300.

Figure 22:
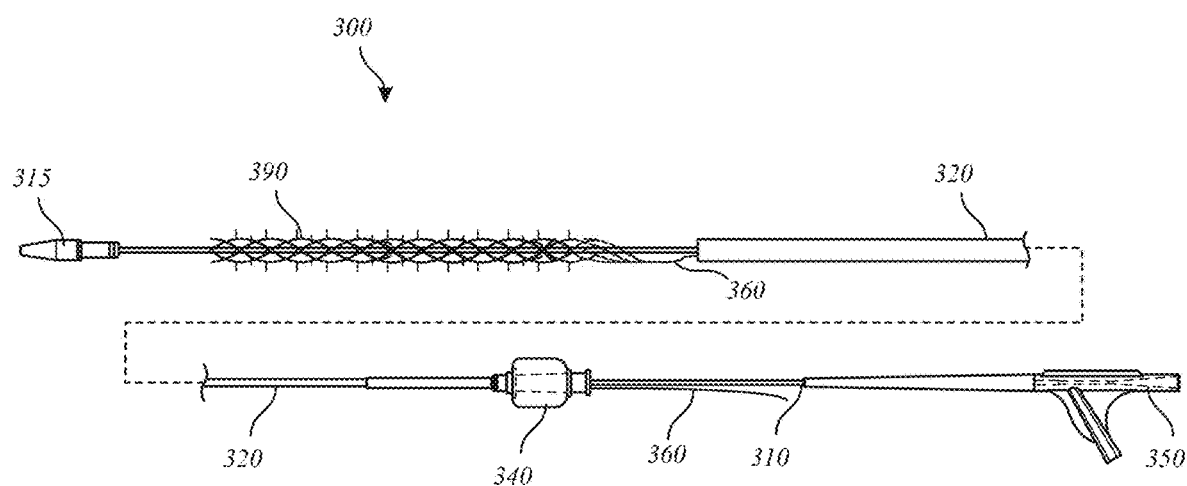
FIG. 22 shows a side view of the delivery system of FIG. 21 in a second stage of deployment.

As shown in FIG. 22, the outer shaft 320 can be moved to unsheath an inflatable balloon 380. For example, once the distal region of the delivery system 300 is positioned at a desired location, the outer shaft 320 is configured to be at least partially proximally retracted relative to the inner shaft 310 by retracting the outer shaft hub 340 relative to the connector 350. Once the outer shaft 320 is partially retracted, a portion of the stent 390 is unsheathed and protruding features 394 of the stent 390 are configured to radially expand outwardly away from the inner shaft 310. The stabilizing wire 360, accessible by a user, is configured engage with the proximal end of the stent 390 and control the position of the stent 390 during and after retraction of the outer shaft 320. The user can secure the stabilizing wire 360 relative to the inner shaft 310 while the outer shaft 320 is retracted so that the position of the stent 390 can be maintained with respect to the inner shaft 310, including the balloon 380, during retraction of the outer shaft 320.

Figure 23:
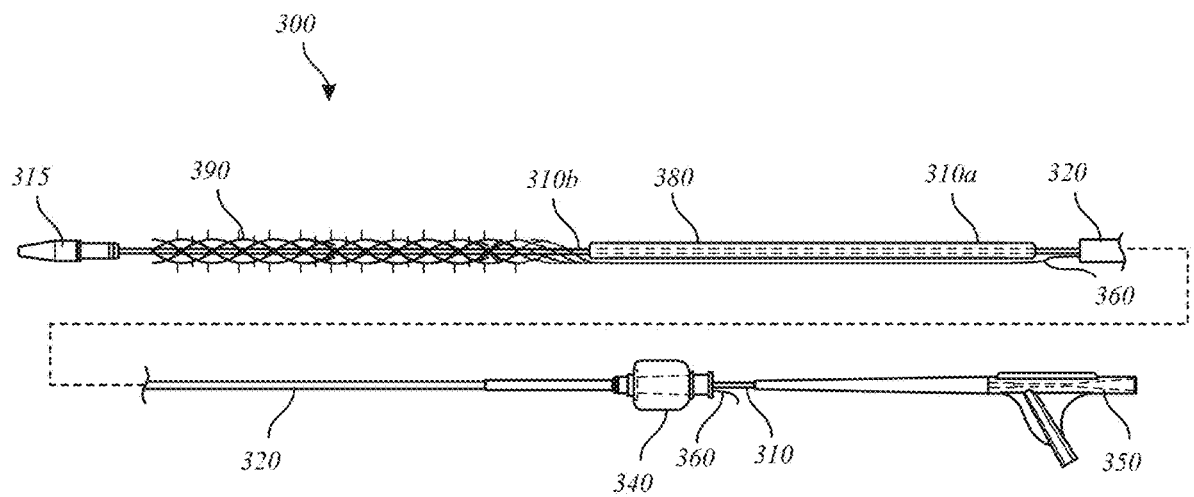
FIG. 23 shows a side view of the delivery system of FIG. 21 in a third stage of deployment.

As shown in FIG. 23, the outer shaft 320 can be further moved to unsheath a balloon 280. Once the outer shaft 320 is further retracted, at least a portion of the balloon 380 is unsheathed. As shown, the balloon 380 is positioned at a proximal portion 310a of the inner shaft 310, and the stent 390 is positioned at a distal portion 310b of the inner shaft 310. The distal portion 310b of the inner shaft 310 can have an outer cross-sectional dimension that is smaller than an outer cross-sectional dimension of the balloon 380, thereby permitting the stent 390 to be collapsed onto the distal portion 310b in a smaller profile than would be achieved if the stent 390 were collapsed onto the balloon 380.

Figure 24:
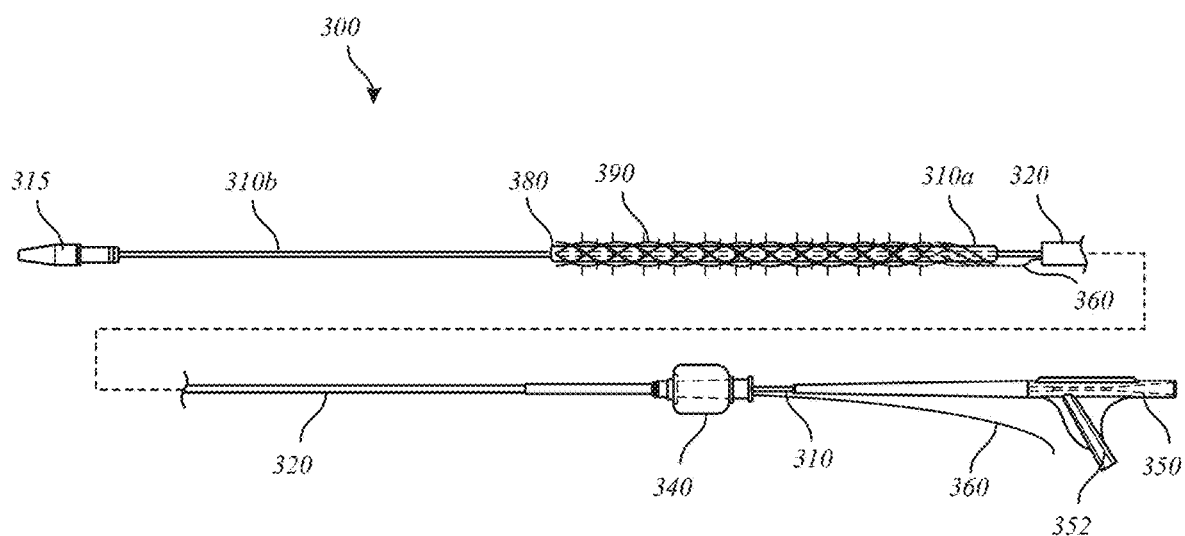
FIG. 24 shows a side view of the delivery system of FIG. 21 in a fourth stage of deployment.

As shown in FIG. 24, when both the stent 390 and the balloon 380 are unsheathed by the outer shaft 320 and exposed, the stent 390 can be axially aligned with the balloon 380. Because the inner shaft 310 extends through the stent 390, distal movement of the inner shaft 310 relative to the stent 390 can achieve axially alignment of the balloon 380 with the stent 390. The balloon 380 can have an axial length that is greater than the axial length of the stent 390, so that an entirety of the stent 390 is overlapping with the balloon 380 when axially aligned.

The balloon 380 can be inflated to expand or further expand the stent 390. For example, an interior region of the balloon can be fluidly connected, via the inner shaft 310, to the port 352 of the connector 350. By providing a fluid through the port 352, the balloon 380 can be expanded, thereby expanding or further expanding the stent 390. The expansion with respect to target anatomy will be further discussed herein.

Following one or more of the above-described operations, the balloon 380 can be deflated. The stent 390 can be maintained for any duration of time in an expanded state. For example, the stent 390 can be maintained for a duration of time effective to provide therapeutic treatment (e.g., remodeling and/or drug delivery) to target anatomy.

Additionally or alternatively, the delivery system 300 can be deployed at multiple locations. The stent 390 can be collapsed by moving the outer shaft 320 over the stent 390. Optionally, the stent 390 can be axially realigned with the proximal portion 310a of the inner shaft 310 prior to collapse by the outer shaft 320. The stent 390 and the balloon 380 can be moved to another target location, and one or more of the above-described operations can be repeated.

Additionally or alternatively, the delivery system 300 can be removed. The stent 390 can be collapsed by moving the outer shaft 320 over the stent 390. Optionally, the stent 390 can be axially realigned with the proximal portion 310a of the inner shaft 310 prior to collapse by the outer shaft 320. Components of the delivery system 300 can be removed from the patient by retracting proximally over the guidewire.

Additionally or alternatively, the stent 390 can be detached from the stabilizing wire 360 and left as an implant within the patient. Following detachment, other components of the delivery system 300 can be removed from the patient by retracting proximally over the guidewire.

As shown in FIGS. 25-28, a delivery system 500 can be provided with a stent 590 that is positioned over an inflatable balloon 580 for expansion and delivery of the stent 590 to a target delivery location. By positioning the stent 590 over and about the inflatable balloon 580, the stent 590 is ready to be expanded by the balloon 580 immediately upon partial or complete unsheathing with respect to the outer shaft 520. Any released portion of a stent 590 can be expanded by an underlying portion of a balloon 580 that is similarly released.

Figure 25:
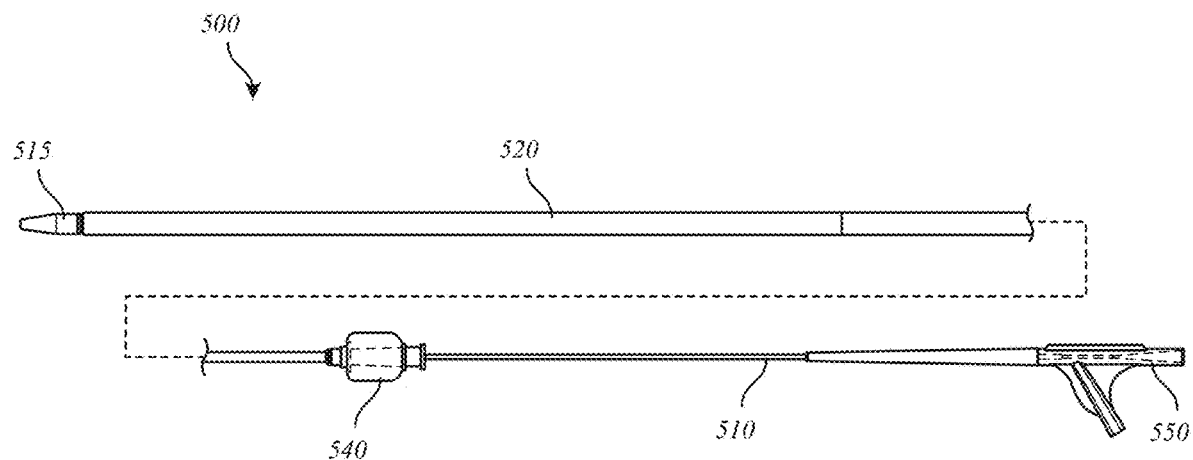
FIG. 25 shows a side view of an example of a delivery system in a first stage of deployment.

As shown in FIG. 25, the delivery system 500 is provided with the outer shaft 520 covering or ensheathing other components of the delivery system 500. For example, the outer shaft 520 can extend to the tip 515 positioned at a distal end of the inner shaft 510. The inner shaft 510 can extend within the outer shaft 520, with a length thereof accessible proximal to a proximal end of the outer shaft 520 (e.g., at the outer shaft hub 540). Additionally or alternatively, the connector 550 can be accessible proximal to a proximal end of the outer shaft 520 (e.g., at the outer shaft hub 540). As discussed above, a guidewire can be advanced ahead of the tip 515 (e.g., through the inner shaft 510) to provide a pathway for advancement of other components of the delivery system 500.

Figure 26:
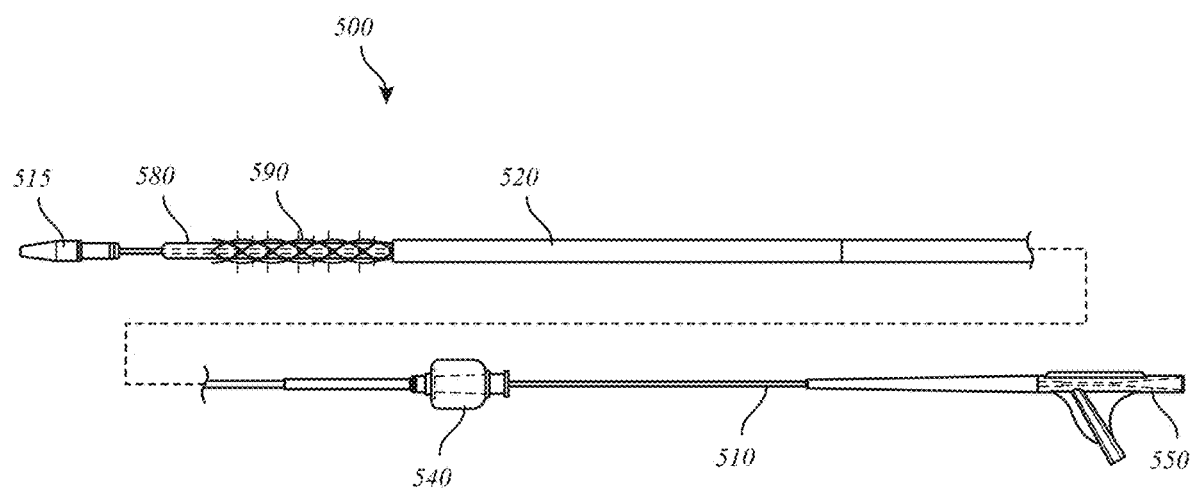
FIG. 26 shows a side view of the delivery system of FIG. 25 in a second stage of deployment.

As shown in FIG. 26, the outer shaft 520 can be moved to unsheath a portion of the stent 590 and other components of the delivery system 500. For example, once the distal region of the delivery system 500 is positioned at a desired location, the outer shaft 520 is configured to be at least partially proximally retracted relative to the inner shaft 510 by retracting the outer shaft hub 540 relative to the connector 550. Once the outer shaft 520 is partially retracted, a portion of the stent 590 and/or the balloon 580 is unsheathed and protruding features 594 of the exposed portion of the stent 590 are configured to radially expand outwardly away from the inner shaft 510.

The stent 590 can be fixedly attached to another component of the delivery system 500, such as the inner shaft 510 (e.g., via an anchor portion). Alternatively, the stent 590 can be adjustably positioned relative to one or more other components of the delivery system 500. For example, the stent 590 can be coupled to a stabilizing wire that is accessible to a user at a proximal end of the delivery system 500, and the user can adjust a position of the stent 590 by operation of the stabilizing wire.

Figure 27:
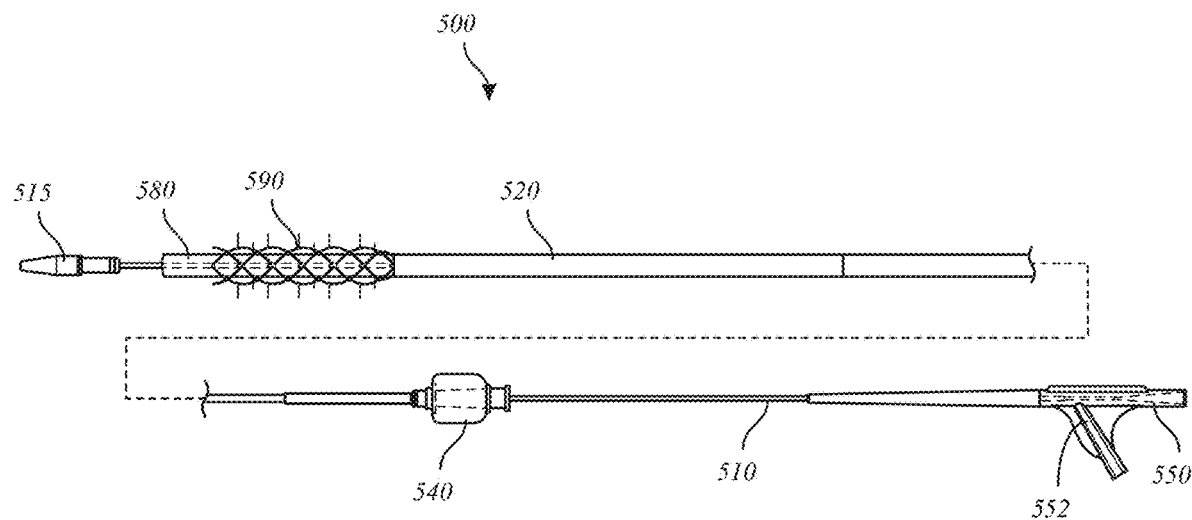
FIG. 27 shows a side view of the delivery system of FIG. 25 in a third stage of deployment.

As shown in FIG. 27, the outer shaft 520 has been partially retracted and the stent 590 is partially unsheathed. The stent 590 can be connected to the inner shaft 510, for example with a stabilizing wire (not shown), as described herein. Accordingly, the position of the stent 590 can be maintained with respect to the inner shaft 510, including the balloon 580. For example, while some adjustment of the length and/or axial position of the stent 590 may occur during radial expansion of the stent 590, it will be understood that the stabilizing wire can maintain the position of at least a portion of the stent 590 to be around and axially aligned with at least a portion of the balloon 580. Additionally or alternatively, the stent 590 can be secured relative to the outer shaft 520 by locking the outer shaft hub 540 relative to the inner shaft 510 at a proximal portion of the delivery system 500. For example, a locking member can be controllably engaged and disengaged to selectively lock relative axial positions and/or movement of the outer shaft hub 540 and the inner shaft 510. Such a locking member, when engaged can prevent proximal retraction of the outer shaft 520 when the balloon 580 is expanded, including portions of the balloon 580 that are within the outer shaft 520. The balloon 580 can have an axial length that is greater than the axial length of the stent 590, so that an entirety of the stent 590 is overlapping with the balloon 580.

An extent to which the stent 590 and/or the balloon 580 are unsheathed (e.g., partially unsheathed) can be determined by one or more of a variety of mechanisms. For example, the stent 590, the balloon 580, the outer shaft 520, and/or one or more other components coupled to one or more of the above can include a visualization marker, such as a radiopaque marker. The position of such components relative to each other and/or a target location can be determined visually, for example by an imaging technique (e.g., angiography). Additionally or alternatively, the relative positions of the stent 590, the balloon 580, and/or the outer shaft 520 can be determined and/or inferred by corresponding components at a proximal end of the delivery system 500. For example, the positions the outer shaft hub 540, the inner shaft 510, and/or a stabilizing wire (not shown) can be compared to determine the relative positions of the outer shaft 520, the balloon 580, and/or the stent 590, respectively. Appropriate markers, detents, or other indicators can be provided on the outer shaft hub 540, the inner shaft 510, and/or a stabilizing wire (not shown) at the proximal end of the delivery system 500 for reference by a user. For example, such markers, detents, or other indicators can be incrementally spaced apart from each other to indicate to the user a position of the outer shaft hub 540 with respect to the inner shaft 510. Such an indication can be correlated with an extent to which the stent 590 is unsheathed.

When both the stent 590 and the balloon 580 are partially unsheathed by the outer shaft 520, the initially exposed portion of the balloon 580 can be inflated to expand or further expand the stent 590. For example, an interior region of the initially exposed portion of the balloon 580 can be fluidly connected, via the inner shaft 510, to the port 552 of the connector 550. By providing a fluid through the port 552, the initially exposed portion of the balloon 580 can be expanded, thereby expanding or further expanding the initially exposed portion of the stent 590. Other portions of the stent 590 and/or the balloon 580 can remain within the outer shaft 520. Expansion can be performed, for example, while the outer shaft 520 is locked relative to the inner shaft 510 (e.g., with the outer shaft hub 540). Such locking can prevent the outer shaft 520 from further retracting in response to forces due to expansion of the partially exposed stent 590 and/or balloon 580. The expansion with respect to target anatomy will be further discussed herein.

Figure 28:
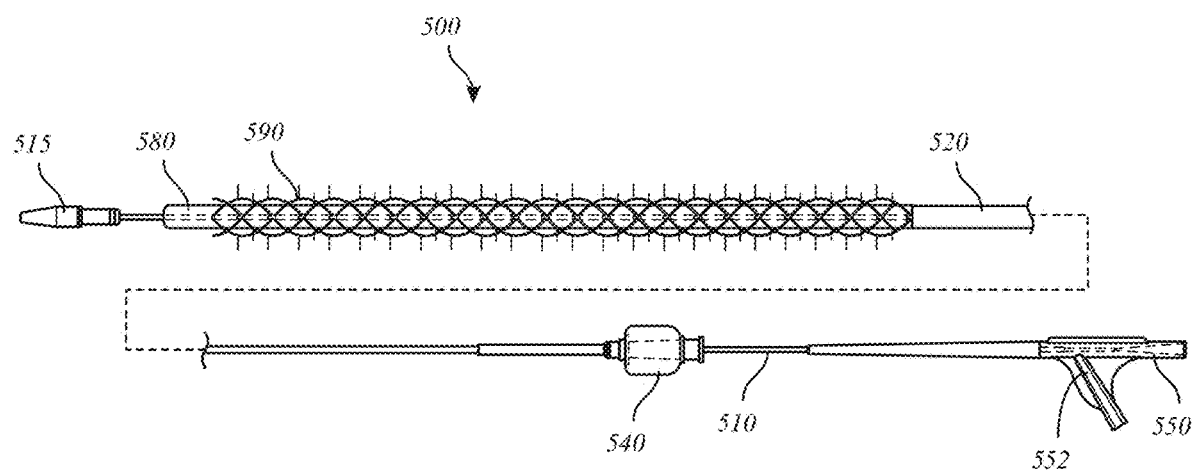
FIG. 28 shows a side view of the delivery system of FIG. 25 in a fourth stage of deployment.

Following an initial deployment, additional operations can be performed to expand the stent 590 in a subsequent stage of the same procedure. For example, a different length and/or portion of the stent 590 can be utilized in a subsequent operation. As shown in FIG. 28, the outer shaft 520 has been further retracted and the stent 590 is further unsheathed. When both the stent 590 and the balloon 580 are more fully unsheathed by the outer shaft 520, the more fully exposed portion of the balloon 580 can be inflated to expand or further expand the more fully exposed portion of the stent 590, for example via the port 552, as discussed herein. Other portions of the stent 590 and/or the balloon 580 can remain within the outer shaft 520. As described above, expansion can be performed while the outer shaft 520 is locked relative to the inner shaft 510 (e.g., with the outer shaft hub 540) to stabilize the system during inflation of the balloon 580.

An extent to which the stent 590 and/or the balloon 580 are unsheathed (e.g., further unsheathed) can again be determined by one or more of a variety of mechanisms, such as those described above with respect to determining an extent of partial unsheathing.

In some embodiments, the operating length of the stent 590 that is unsheathed, exposed, and/or expanded in the operations described above can be of different lengths. For example, the operating length can be shorter in an initial stage and longer in a subsequent stage. Alternatively, the operating length can be longer in an initial stage and shorter in a subsequent stage.

Where different operating lengths are desired, the balloon 580 can optionally include multiple segments that are independently inflatable. For example, the balloon 580 can include multiple segments that are aligned at different axial locations along the inner shaft 510. The inner shaft 510 can provide multiple lumens each connecting to corresponding ports. A fluid can be provided through a selected number of the ports to inflate only the corresponding balloon segments. For example, only the balloon segments that are outside of the outer shaft 520 can be inflated to expand corresponding portions of the stent 590. Additionally or alternatively, the balloon segments can be in fluid communication with each other such that they are inflated in a sequence.

Between an initial expansion (e.g., the expansion illustrated in FIG. 27) and a subsequent expansion (e.g., the expansion illustrated in FIG. 28), the stent 590 and/or the balloon 580 can be deflated, compressed, and/or at least partially retracted into the outer shaft 520. Alternatively, the stent 590 and/or the balloon 580 can be further exposed by unlocking the outer shaft 520 from the inner shaft 510 and allowing the outer shaft 520 to further retract in response to forces from the inflated balloon 580.

The transition from an initial expansion to a subsequent expansion can be performed to adjust an operating length of the stent 590 to more fully address a target region. For example, an initial operating length of the stent 590 can be exposed and expanded. The user can then evaluate the effectiveness of the operation (e.g., via imaging technique such as angiography). Where the initial operating length of the stent 590 is determined to be insufficient, the stent 590 and/or the balloon 580 can be further exposed to increase the operating length of the stent 590. Such adjustments can be made as needed until an adequate operating length is provided. It will be recognized that the ability to perform such adjustments may avoid the need to remove a stent that is discovered to be inadequate and replace it with a different stent or other device that provides an adequate operating length. By eliminating these steps, total operation time can be reduced. Additionally, a user can desire to deploy a device with an operating length that is adequately long (e.g., to span a target region) without being longer than is required (e.g., to avoid operating on regions outside the target region). It will be recognized that the user can provide a single stent 590 with an adjustable operating length to adequately address a target region that has an initially uncertain length or where the required operating length of the stent is otherwise unknown or uncertain. Such capabilities reduce the burden on the user to accurately select the devices with the correct operating length at the beginning of an operation. Furthermore, the capabilities described herein also reduce the need to provide a wide array of devices that provide different performance characteristics, as a single device or reduced number of devices can be operated as described herein to provide a desirably wide range of performance characteristics.

The transition from an initial expansion to a subsequent expansion can be performed to address different operating length requirements of different target regions. Between an initial expansion and a subsequent expansion, the stent 590 and/or the balloon 580 can be repositioned to a different location. For example, the stent 590 can be repositioned to align with a different target region. Where the new target region has a different length or other feature relative to an initial target region, the operating length of the stent 590 can be selected and/or modified accordingly to adequately address each of the target regions. It will be recognized that the ability to perform such adjustments may avoid the need to remove a stent suitable for an initial target region and replace it with a different stent that is suitable for a different target region. By eliminating these steps, total procedure time can be reduced, thereby reducing risks associated with long procedure times. Additionally, it will be recognized that the user can provide a single stent 590 with an adjustable operating length to adequately address each of different target regions despite each target region having potentially different requirements for an operating length of the stent 590. This allows a user with greater flexibility and options throughout a procedure with a single device.

Following one or more of the above-described operations, the balloon 580 can be deflated. The stent 590 can be maintained for any duration of time in an expanded state. For example, the stent 590 can be maintained for a duration of time effective to provide therapeutic treatment (e.g., remodeling and/or drug delivery) to target anatomy and allows fluid flow through the expanded stent and deflated balloon where there is no fluid blockage through the treated site.

Additionally or alternatively, the delivery system 500 can be deployed at multiple locations. The stent 590 can be collapsed by moving the outer shaft 520 over the stent 590. The stent 590 and the balloon 580 can be moved to another target location, and one or more of the above-described operations can be repeated.

Additionally or alternatively, the delivery system 500 can be removed. The stent 590 can be collapsed by moving the outer shaft 520 over the stent 590. Components of the delivery system 500 can be removed from the patient by retracting proximally over the guidewire.

Additionally or alternatively, the stent 590 can be detached from the inner shaft 510 and left as an implant within the patient. Following detachment, other components of the delivery system 500 can be removed from the patient by retracting proximally over the guidewire.

Figure 29:
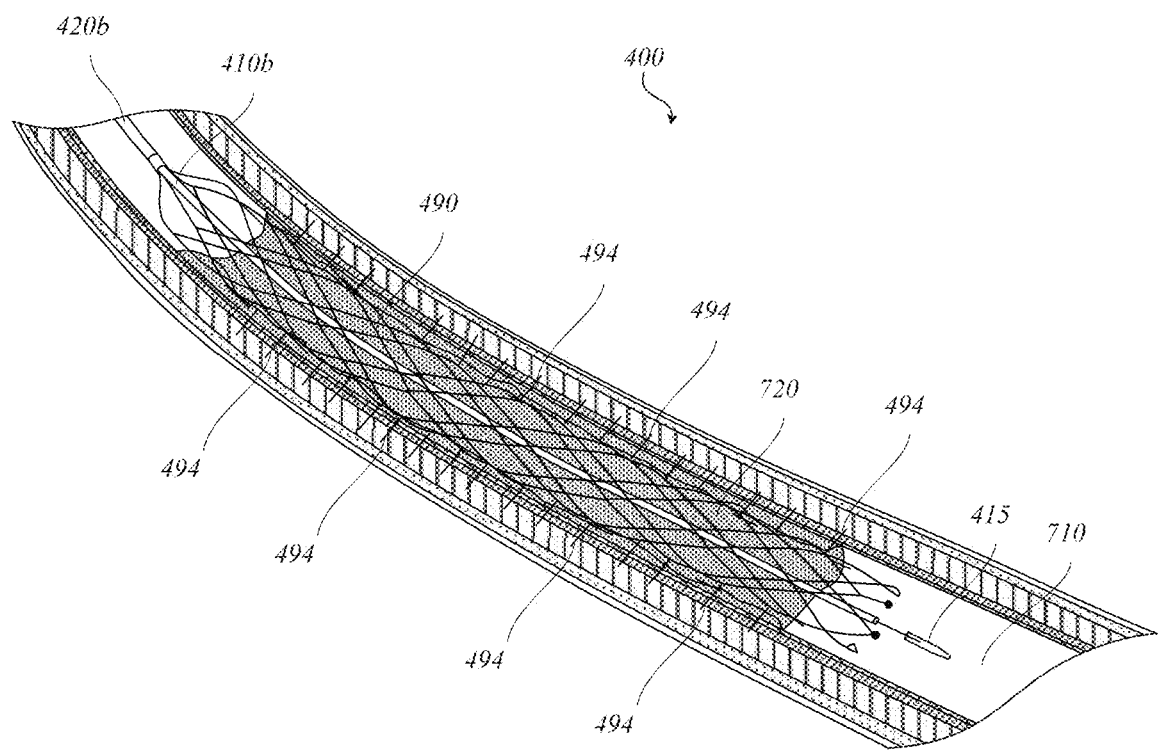
FIG. 29 shows a side view of an example of a delivery system in the delivery state within a body lumen.

Referring now to FIGS. 29-32, an example of a delivery system 400 is shown in various configurations to deliver, position, deploy, and/or recapture a stent. The operations described with respect to the delivery system 400 can be applied to the delivery system 100, the delivery system 200, the delivery system 300, and/or the delivery system 500. As shown in FIG. 29, the delivery system 400 is in a delivery state within a body lumen 710 (e.g., a blood vessel) of a human patient. In this embodiment, the delivery system 400 is configured for intraluminal (e.g., intravascular) delivery through the blood vessel, (e.g., femoral artery) of a human patient. The femoral artery can be accessed by introducing a sheath (e.g., 5F or 6F) into the lumen of the femoral artery. The delivery system 400 is delivered into the body lumen by tracking the distal portion 410*b* of the inner sheath over the guidewire and distally advancing the delivery system 400 to a desired location 720 within the vessel. In some embodiments, an angioplasty procedure is performed at the desired location 720 before the delivery system 400 is advanced to the desired location 720.

Once the delivery system 400 is positioned at the desired location 720, the distal portion 420*b* of the outer sheath is proximally retracted to unsheath the stent 490. In the illustrated embodiment, the body of the stent 490 is at least partially expanded when unsheathed and the protruding features 494 are collapsed. However, the protruding features 494 can be configured to expand once the distal portion 420b of the outer sheath is retracted. In other embodiments, the stabilizing wire (not shown) can be distally advanced and fixed, such as held or pinned, or fixed at the desired location to position the stent before, during, and/or after the outer sheath is proximally retracted to deploy the stent. As illustrated, the tip 415 of delivery system 400 is positioned distally from the distal end of the stent and the inner shaft 410 remains positioned within at least a portion of the lumen of the stent 190.

Figure 30:
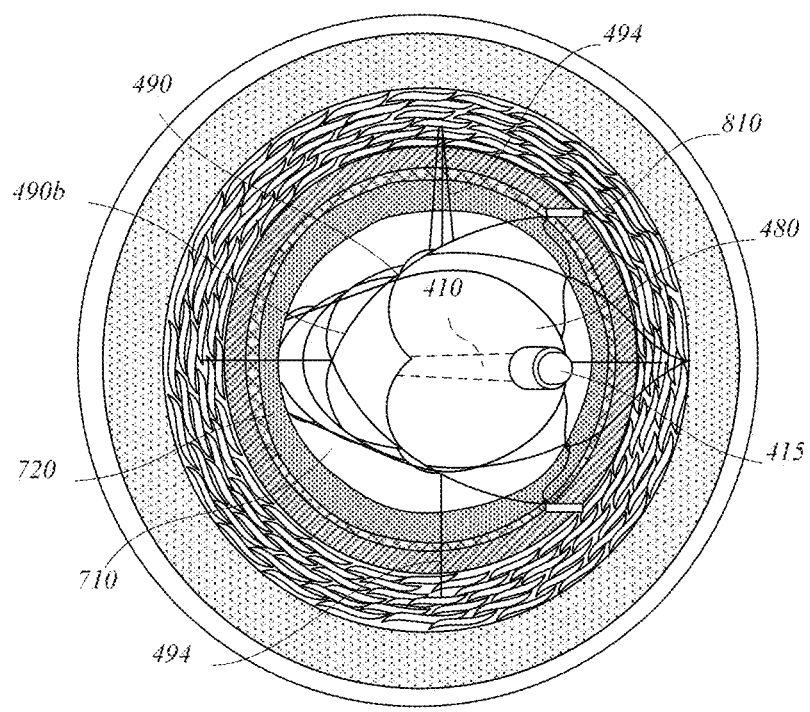
FIG. 30 shows a cross-sectional view of the delivery system of FIG. 29 in a deployed state.

In the deployed state, the protruding features 494 of the stent 490 are configured to expand radially and are further configured to pierce the lumen wall at the desired location once the deployed stent 490 is expanded into contact with the vessel wall (see FIGS. 29 and 30). As will be explained in greater detail below, stents and other expandable structures can be configured to at least partially self-expand, such as expanding outwardly from the collapsed/delivery state to the deployed and/or expanded state when the stents and other expandable structures are at least partially unsheathed from the outer shaft. In some embodiments, stents and other expandable structures are configured to expand when operably coupled with an expandable element or mechanism, such as a balloon. In additional embodiments, self-expanding stents and other structures are configured to further expand when coupled to the expansion mechanism. Regardless of whether the stents and other expandable structures are self-expanding or expand when coupled to the expandable element, the stents and others expandable structures can be configured to expand radially (symmetrically or asymmetrically). In some embodiments, the at least partially expanded stents and other expandable structures can be configured to position at least some of the protruding features perpendicular to the vessel wall.

As shown in FIGS. 29 and 30, the delivery system 400 is configured for insertion of a balloon 480 coupled to the inner shaft 410. The balloon 480 is further configured to be positioned within the stent lumen and expanded therein to further expand the stent 490 between the delivery state and the expanded, deployed state. In some embodiments, the balloon 480 can be coated with a drug-delivery coating and a drug, such as the coatings and drugs described herein. As further discussed elsewhere herein, the stent 490 can be operatively coupled to an actuation mechanism, such as a mechanical actuation mechanism (e.g., stabilizing wire, stent pull wire, pusher shaft, or a combination thereof), configured to position, expand, retract, re-position, and/or remove the stent 490 from the body lumen.

FIG. 30 shows a cross-sectional view of a region of the delivery system 400 in the deployed state within the body lumen. As shown in FIG. 30, the stent 490 is expanded within the vessel by a balloon 480. To expand the deployed stent 490, the balloon 480 is coupled to inner shaft 410 and distally advanced into a lumen of the deployed stent 490 until a distal tip 415 of the inner shaft 410 is positioned near a distal end 490b of the deployed stent 490. As illustrated, the distal end 490b of the stent 490 can include radiopaque markers 490c. Additionally or alternatively, radiopaque markers 490c may be located elsewhere in the delivery system 400, or may be omitted from the delivery system 400.

Figure 31:
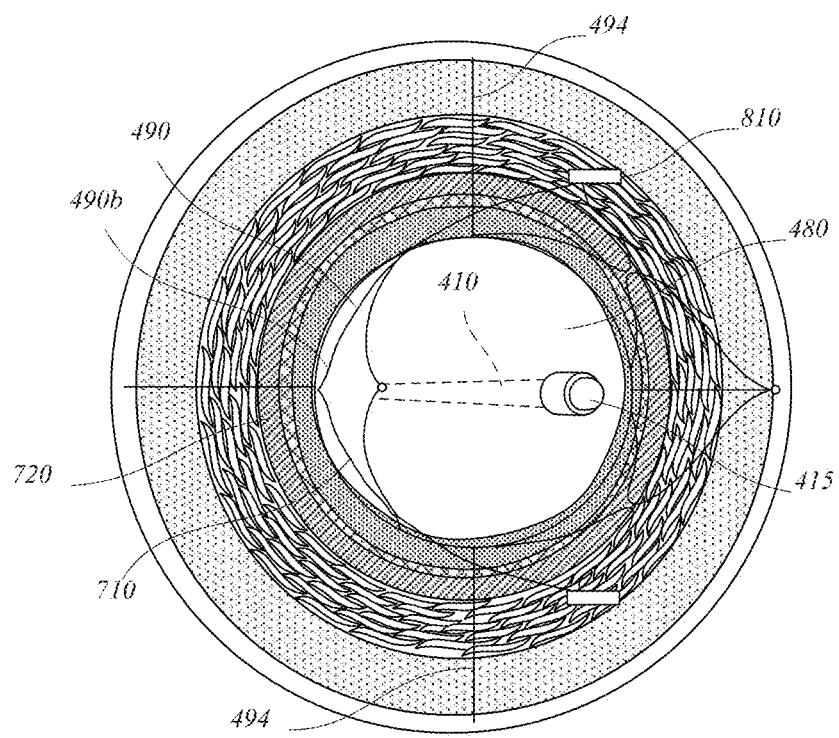
FIG. 31 shows a cross-sectional view of the delivery system of FIG. 29 with a balloon and a stent in an expanded state within a body lumen.

FIG. 31 shows a cross-sectional view of a portion of the delivery system 400 in a deployed state with the stent 490 having protruding features 494 expanded within and piercing a portion of the vessel wall. As illustrated in FIG. 31, the balloon 480 is deployed and radially expanded to engage with and further expand the stent 490 into contact with the lumen vessel. When the stent 490 is expanded, the protruding features 494 penetrate further into the wall.

Figure 32:
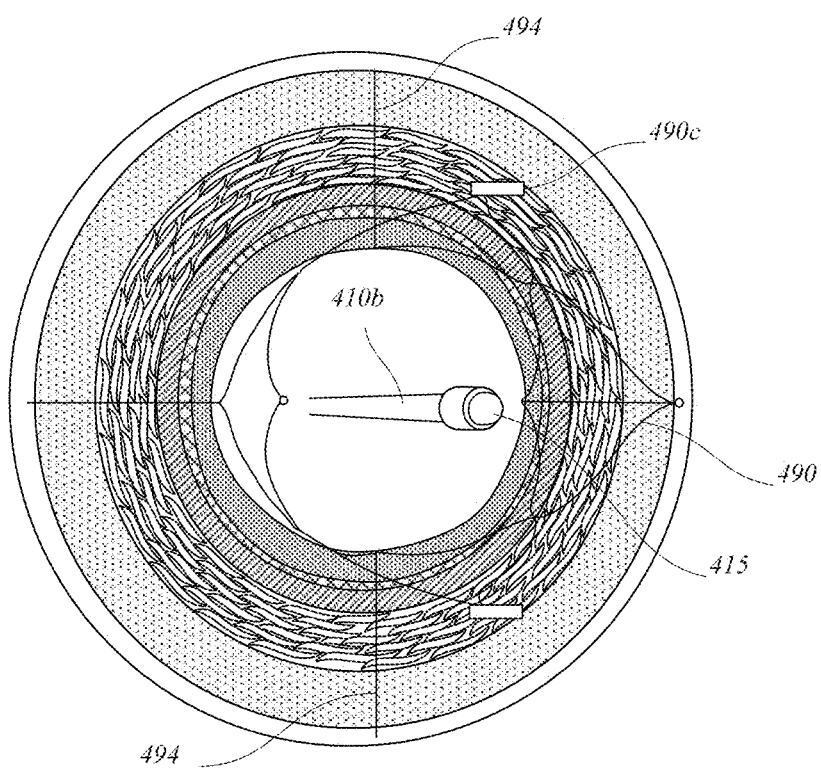
FIG. 32 shows a cross-sectional view of a region of the delivery system of FIG. 29 with a stent in a treatment state and a balloon in a collapsed state that allows for fluid flow.

FIG. 32 shows a cross-sectional view of the delivery system 400 in a treatment state. In the treatment state, the balloon 480 has been deflated. As illustrated, the distal portion 410b of the inner shaft 410 remains in the body lumen. Following deflation of the balloon 480, the stent 490 remains expanded into contact with the lumen wall and the protruding features 494 remain penetrated into the wall. Any drugs carried by the protruding features 494 are at least partially released into the body lumen wall at the treatment state. Optionally, the stent 490 can be affixed to the balloon 480, such as by crimping the stent 490 to at least partially surround the balloon 480, such that the stent 490 is both expanded and collapsed by inflating and deflating the balloon 480, respectively.

While the stents described herein have the features shown, it will be understood that a variety of different stents and other devices can be used with the delivery systems described herein. Various features are set forth below by way of example, and not by limitation.

Regarding such stents and other devices, the material(s) for forming the frame, struts, and/or protruding features described herein can be selected based on mechanical and/or thermal properties, such as strength, ductility, hardness, elasticity, flexibility, flexural modulus, flexural strength, plasticity, stiffness, emissivity, thermal conductivity, specific heat, thermal diffusivity, thermal expansion, any of a variety of other properties, or a combination thereof. If formed from a material having thermal properties, the material can be activated to deliver thermal treatment to the desired treatment site. Regardless of the material, the frame, struts, and/or protruding features can be formed from a tube or a wire, such as a solid wire, by laser cutting or other suitable techniques. When formed from the wire, a portion of the wire can be removed by chemical etching or another suitable method to create an inner dimension of the stent.

Stents (e.g., the frame and the struts) can be sized and shaped for placement within various body lumens, including blood vessels, while not rupturing the vessel. For example, several stents and other structures can have radial strength that allows for features of the body lumen (e.g., vessel wall) to receive drugs without dissection or damage thereto. Vessels in which the stents described herein may be sized and shaped for placement include arteries, such as coronary arteries, peripheral arteries, carotid arteries, circle of willis, anterior cerebral artery, middle cerebral artery, posterior cerebral artery, any of the lenticulostriate arteries, renal arteries, femoral arteries, veins, such as cerebral veins, saphenous veins, arteriovenous fistulas, or any other vessel that may contain a treatment site. Stents can have a variety of shapes, including a cube, a rectangular prism, a cylinder, a cone, a pyramid, or variations thereof.

Stents and other structures having protruding features can include a variety of dimensions (in both the low-profile delivery state and expanded deployed state). These embodiments can provide for expansion that enables usage in a variety of situations covering a wide range of dimensions, such as to treat and/or prevent dissection. Regardless of the shape, stents can have a length of about 0.25 mm, about 0.5 mm, about 1 mm, about 2 mm, about 3 mm, about 4 mm, about 5 mm, about 6 mm, about 7 mm, about 8 mm, about 9 mm, about 10 mm, about 12 mm, about 14 mm, about 16 mm, about 18 mm, about 20 mm, about 30 mm, about 40 mm, about 50 mm, about 60 mm, about 70 mm, about 80 mm, about 90 mm, or about 100 mm. In addition, a stent shaped into a cube, a rectangular prism, or a pyramid can have a width of about 0.25 mm, about 0.5 mm, about 1 mm, about 2 mm, about 3 mm, about 4 mm, about 5 mm, about 6 mm, about 7 mm, about 8 mm, about 9 mm, about 10 mm, about 12 mm, about 14 mm, about 16 mm, about 18 mm, about 20 mm, about 25 mm, or about 30 mm. Moreover, a stent shaped into a cylinder or a cone can have a diameter of about 0.25 mm, about 0.5 mm, about 1 mm, about 2 mm, about 3 mm, about 4 mm, about 5 mm, about 6 mm, about 7 mm, about 8 mm, about 9 mm, about 10 mm, about 12 mm, about 14 mm, about 16 mm, about 18 mm, about 20 mm, about 25 mm, about 30 mm, about 35 mm, about 40 mm, or about 50 mm. The width or the diameter of the stent can decrementally decrease along a length of the stent. In addition, the stent can be sized and shaped to prepare the body lumen for certain procedures, such as a stent placement procedure.

A stent and/nor other expandable structures in the expanded state can have a cross-sectional dimension of about 2 mm to about 10 mm, inclusive of the expanded protruding features. For example, a frame can have a cross-sectional dimension of about 1 mm to about 9 mm and the protruding features can each have a length from about 0.1 mm to about 1.5 mm. In some embodiments, the stent has an overall cross-sectional dimension of about 4 mm with the frame having a cross-sectional dimension of about 2 mm and the protruding features each having a length of about 1 mm. In some embodiments, the stent has an overall cross-sectional dimension of about 6 mm with the frame having a cross-sectional dimension of about 4 mm and the protruding features each having a length of about 1 mm. In further embodiments, the protruding features can have a plurality of lengths such that the length of the protruding features of a stent or other expandable structure differs. For example, a stent can include protruding features having a length of about 0.2 mm, about 0.5 mm, and about 1 mm.

Profiles of the stents or other structures can be sized such that the stents or other structures are compatible with a wide range of catheter sizes. Embodiments in accordance with the present technology can include stents or other structures designed to receive a guidewire, such as guidewires having a diameter of 0.010, 0.014, 0.018, 0.035, or 0.038 inch. In several embodiments, the stent or scaffold structure can be sized and designed for delivery via a micro-catheter that it is pushed through. In some embodiments, stents or structures can be incorporated into a delivery system, including modular or single unit delivery systems.

Stents and other structures described herein can include a marking for visualization of the stent within the body lumen, such as one or more radiopaque markers. The radiopaque markers can be formed from Clearfil Photo Core PLT®, tantalum, titanium, tungsten, barium sulfate, and zirconium oxide, or another suitable radiopaque marking. The markings can be formed on a proximal portion of the stent, a distal portion, an intermediate portion, or a combination thereof. The markings can be a band, a coil, a clip, filled into one or more portions of a tube in the stent, plated onto one or more portions of the stent, or a combination thereof. Regardless of the type of marking, the marking can be coined, swaged, wrapped, or encased along, or onto any portion of the stent.

Stents and other structures can be flexible enough to track through various anatomical features, including those having a curvature. The flexible properties of the stent and other structures can be provided by the material from which they are formed. In addition, flexible properties can also be provided by fracturing one or more of the members engaging with and extending between two or more rows of struts. Additionally, the stent or other structure can be readily deployed and expanded, and retracted and contracted. The stent or other structure can also be readily repositioned within a vessel or other body lumen.

In several embodiments, a drug-eluting compound is coated onto at least a portion of the protruding features, the frame, the struts, and/or the balloon. The coating can be any suitable coating known to one of ordinary skill in the art suitable to deliver the drug to the wall. For example, suitable coatings include, but are not limited to a snow coating or a crystalline coating having edges configured to remain in the wall. The drug-eluting compound can be a synthetic or biological polymer coated into a variety of different patterns and thicknesses suitable for delivering the drug contained therein. In other embodiments, the protruding features themselves may be composed of drug-eluting materials. The drug carried by the drug-eluting compound and/or the protruding features in accordance with the present technology can be any drug suitable for treating the treatment site in which the stent will be placed and may or may not include an excipient. For example, the drug can be an anti-proliferative, an anti-neoplastic, a migration inhibitor, an enhanced healing factor, an immunosuppressive, an anti-thrombotic, a blood thinner, or a radioactive compound. Examples of anti-neoplastics include, but are not limited to, siroliums, tacrolimus, everolimus, leflunomide, M-prednisolone, dexamethasone, cyclosporine, mycophenolic acid, mizoribine, interferon, and tranilast. Examples of anti-proliferatives include, but are not limited to, taxol/paclitaxel, actinomycin, methotrexate, angiopeptin, vincristine, mitmycine, statins, c-myc anti sense, Abbot ABT-578, RestinASE, 2-chlorodeoxyadenosine, and PCNA ribozyme. Examples of migration inhibitors, but are not limited to, include batimistat, prolyl hydrosylase, halofunginone, c-preteinase inhibitors, and probucol. Examples of enhanced healing factors include, but are not limited to, BCP 671, VEGF, estradiols, NO donor comounds, and EPC antibodies. Examples, of radioactive compounds include, but are not limited to, strontium-89 chloride (Metastron®), samarium-153 (Quadramet®), radium-223 dichloride (Xofigo®), yttrium-90, and iodine-131. In some embodiments, the drug-eluting compound and/or the protruding features can carry more than one drug.

In some embodiments, the protruding features can include textured (e.g., ribbed) surfaces which is expected to provide greater surface area for drug-delivery. Moreover, any protruding features can include a textured surface such as a ribbed surface (vertical, horizontal, radial, or circular relative to a longitudinal plane of the protruding feature), a cross-hatched surface, an isotropic surface, or other surface types suitable for providing greater surface area for drug-delivery.

The protruding features can be sized and shaped to engage with and/or penetrate an occlusion, a neointima, an intima, an internal elastic lamina (IEL) a media, an external elastic lamina (EEL), an adventitia, or a combination thereof. The protruding features can also be sized and shaped to engage with and/or penetrate a tissue and/or structure adjacent to the body lumen in which the stent is to be placed while not rupturing the body lumen. For example, the stent can include square protruding features sized and configured to penetrate into the intima and/or the media of a body lumen, pointed protruding features sized and configured to penetrate and extend into the media, and/or the IEL. In addition, protruding features can be configured to bend in one or more directions relative to a longitudinal axis of the stent to engage with and/or penetrate a portion of the body lumen described herein. In several embodiments, the protruding features can penetrate deeper into the wall of a diseased body lumen, such as a vessel, compared to a stent lacking protruding features. In addition, the stent can allow for blood to flow even while in the expanded position and with drug-eluting on-going.

Various protruding features described herein can deliver drugs deeper into a vessel wall than possible via angioplasty balloons or other existing devices. In addition to carrying one or more drugs for treatment of the site, the protruding features can also carry a molecule suitable for degrading a portion of the occlusion, neointima, and/or intima to allow the protruding features to penetrate deeper in to the vessel wall than without the molecule. For example, the molecule suitable for degradation can be an enzyme, such as elastase, collagenase, or a proteinase, such as, metalloproteinases, serine proteinases, cysteine proteinases, extracellular sulfatases, hyaluronidases, lysyl oxidases, lysyl hydroxylases, or a combination thereof.

Further, it will also be appreciated that stents can carry one or more protruding features on one or more portions of the stent. For example, the stents can carry about 5 protruding features, about 10 protruding features, about 15 protruding features, about 20 protruding features, about 30 protruding features, about 40 protruding features, about 50 protruding features, about 60 protruding features, about 70 protruding features, about 80 protruding features, about 90 protruding features, or about 100 protruding features. The protruding features can be carried by the frame, the struts, or a combination thereof. The number of protruding features can vary depending upon, for example, the target treatment site, the type of drug being delivered, and size of the stent, etc. In addition, the protruding features carried by the stent can be different types of the protruding features disclosed herein.

In some embodiments, once positioned against a body lumen wall (e.g., a vessel wall), tissue and/or fluid can interact with the protruding feature to dissolve the drug and selectively release it from the reservoir. In other embodiments, the protruding feature can be configured to deliver the drug via a variety of means once the stent is expanded. Protruding features are accordingly expected to provide an effective means for selectively delivering a drug to a desired location, while reducing inadvertent loss or release of drugs. In other embodiments, the stent can include more than one protruding feature, or a protruding feature having more than one reservoir. In several embodiments, the stent including protruding features can have the protruding feature, such as the coating or the reservoir, concealed (e.g., recessed) until the stent is positioned at the treatment site. Once positioned at the target site, the protruding feature can be revealed (e.g., expanded/projected, etc.) during and/or after expansion of the stent. This is expected to reduce any loss of the drug carried by the protruding feature during delivery to the treatment site.

In some embodiments, the stents can further include a material (e.g., PTFE, Dacron, polyamides, such as nylon and/or polyurethane based materials, silicone, etc.) positioned over a stent, scaffold or other structure having protruding features covering at least a portion of the outer surface area. In some embodiments, the material covers the entire outer surface area. The material can be a mesh or a braid. In some embodiments, the material can be configured to increase a surface area of the stent useful for providing additional surface area of the stent for coating with a drug. In other embodiments, the material can further be configured to allow blood flow through the inner diameter of the stent and/or limit blood flow to an outer dimension of the stent. In additional embodiments, the material can create a barrier between fluid flow (e.g., blood flow) and the drug-delivery locations. In addition, the material can be configured to prevent debris from the wall of the body lumen from entering the bloodstream. In such embodiments, the associated systems and devices can be used for temporary dissection tacking or coverage of a region that may have been perforated during a procedure.

The embodiments described herein provide delivery systems for one or more structures having a means for delivering drugs to a specific region within a body lumen, such as the vasculature, while still allowing fluid (e.g., blood) to flow through the treatment area where the structure has been placed and/or other devices or treatment means within the adjacent body lumen. In some embodiments, the fluid is temporary prevented from flowing through the treatment area while one or more regions of systems is delivered, deployed, positioned, and/or removed from the body lumen. In addition, the delivery systems can be configured to prepare the body lumen for treatment, by raking the stent, pulling the stent, turning the stent, or a combination thereof, proximal or distal to the treatment site. In other embodiments, the delivery systems can be configured to rotate the stent when mechanical force is applied.

The systems disclosed herein can provide for adjustment, recapture, and/or redeployment of the associated stents or other structures, and/or deployment of a different stent or other structure, allowing a practitioner to more effectively to treat a desired region more accurately and deliberately. In several embodiments, the stent or other delivery structure can be deployed for a temporary period (e.g., for less than 24 hours), and then retracted and removed. In these embodiments, the protruding features can engage with and/or pierce the lumen wall and remain therein after the stent or other delivery structure is removed, or can be retracted and removed with the stent or other delivery structure. The stent can be configured to self-expand, or partially self-expand, when deployed from the delivery system and also be configured to further expand within the body lumen when the balloon is expanded therein. The stent can also be configured to post-dilate when removed from the body lumen. In other embodiments, the stent or other delivery structure can be deployed for a long-term temporary period (e.g., for less than 2 weeks, less than one month, less than 6 months, less than one year), and then retracted and removed. In some embodiments, a different stent or delivery structure can be deployed after a first stent or delivery structure has been retraced and removed. The duration of deployment and duration after removal before deployment of the different stent or delivery structure can vary from minutes, to hours, to days, to weeks, to months, or to years. In these embodiments, removal of the first stent or delivery structure and deployment of a different stent or delivery structure can occur once, twice, three times, four times, five times, six times, seven times, eight times, nine times, or ten times. Moreover, the embodiments described herein can allow for a lower profile system than currently available systems.

In the embodiments described herein and other embodiments configured in accordance with the present technology, stents and other expandable structures may include non-protruding features, such as deployable and/or expandable features, that are not configured for delivering a drug to a target location. For example, stents and other expandable structures configured in accordance with the present technology can include one or more protruding features, one or more non-protruding features, or combinations thereof.

While many embodiments of the stents and/or structures described herein include stents, additional embodiments of the expandable elements, such as stents and/or structures, can include non drug-eluting stents and/or non drug-eluting structures. In these embodiments, the non drug-eluting stents may include one or more protruding members, such as spikes. The spikes can be configured to engage with and/or penetrate a portion of the body lumen or vessel. For example, the spikes can penetrate the vessel wall, thereby reducing and/or eliminating an elasticity of the vessel wall. In these embodiments, the protruding members can be configured to prevent the vessel wall from progressing inward toward the body lumen and restricting and/or constricting flow therein. The protruding members can be integrally formed with the struts, or disposed on the surface of the struts, extending radially outward from the struts toward the target tissue.

Various examples of aspects of the disclosure are described below as clauses for convenience. These are provided as examples, and do not limit the subject technology.

Clause A: a delivery system comprising: an outer shaft; an inner shaft slideably disposed within the outer shaft and comprising an inflatable balloon; a guidewire slideably disposed within the inner shaft; and a stent disposed around the balloon and fixedly coupled to the inner shaft.

Clause B: a method for delivering a stent within a body lumen of a patient, the method comprising: delivering an outer shaft ensheathing an inner shaft and a stent to a target treatment site within the body lumen of the patient, the stent being disposed around a balloon of the inner shaft and fixedly coupled to the inner shaft; proximally retracting the outer shaft to at least partially unsheath the stent; radially expanding the stent to an expanded state by expanding the balloon; and piercing through a portion of a wall of the body lumen with one or more protruding features of the stent.

Clause C: a delivery system comprising: an outer shaft; an inner shaft slideably disposed within the outer shaft and comprising an inflatable balloon on a distal portion of the inner shaft; a guidewire slideably disposed within the inner shaft; and a stent slideably disposed within the outer shaft and on a proximal portion of the inner shaft that is proximal to the balloon, the stent being connected to a stabilizing wire that is slideably disposed within the outer shaft.

Clause D: a method for delivering a stent within a body lumen of a patient, the method comprising: delivering an outer shaft ensheathing an inner shaft and a stent to a target treatment site within the body lumen of the patient, the stent being slideably disposed within the outer shaft and on a proximal portion of the inner shaft that is proximal to a balloon of the inner shaft; proximally retracting the outer shaft to at least partially unsheath the stent and the balloon; moving the inner shaft proximally relative to the stent until the stent is axially aligned with the balloon; radially expanding the stent to an expanded state by expanding the balloon; and piercing through a portion of a wall of the body lumen with one or more protruding features of the stent.

Clause E: a delivery system comprising: an outer shaft; an inner shaft slideably disposed within the outer shaft and comprising an inflatable balloon on a proximal portion of the inner shaft; a guidewire slideably disposed within the inner shaft; and a stent slideably disposed within the outer shaft and on a distal portion of the inner shaft that is distal to the balloon, the stent being connected to a stabilizing wire that is slideably disposed within the outer shaft.

Clause F: a method for delivering a stent within a body lumen of a patient, the method comprising: delivering an outer shaft ensheathing an inner shaft and a stent to a target treatment site within the body lumen of the patient, the stent being slideably disposed within the outer shaft and on a distal portion of the inner shaft that is distal to a balloon of the inner shaft; proximally retracting the outer shaft to at least partially unsheath the stent and the balloon; moving the inner shaft distally relative to the stent until the stent is axially aligned with the balloon; radially expanding the stent to an expanded state by expanding the balloon; and piercing through a portion of a wall of the body lumen with one or more protruding features of the stent.

Clause G: a method for delivering a stent within a body lumen of a patient, the method comprising: delivering an outer shaft ensheathing an inner shaft and a stent to a target treatment site within the body lumen of the patient, the stent being disposed around a balloon of the inner shaft and fixedly coupled to the inner shaft; proximally retracting the outer shaft to partially unsheath the stent; radially expanding a first length of the stent to an expanded state by expanding the balloon while a portion of the stent is within the outer shaft until one or more protruding features of the stent pierces through a first portion of a wall of the body lumen; proximally retracting the outer shaft to further unsheath the stent; and radially expanding a second length of the stent to an expanded state by expanding the balloon until one or more protruding features of the stent pierces through a second portion of the wall of the body lumen.

One or more of the above clauses can include one or more of the features described below. It is noted that any of the following clauses may be combined in any combination with each other, and placed into a respective independent clause, e.g., clause A, B, C, D, E, F, or G.

Clause 1: a connector at a proximal end of the inner shaft, the guidewire extending through the connector, the connector comprising a port in fluid communication with the balloon; and an outer shaft hub at a proximal end of the outer shaft, the inner shaft extending through the outer shaft hub.

Clause 2: incrementally spaced markers on a proximal portion of the inner shaft, wherein the outer shaft hub is slidable over the inner shaft along the proximal portion.

Clause 3: a locking member configured to lock the outer shaft hub to a proximal portion of the inner shaft such that a position of the outer shaft relative to the inner shaft is maintained when the balloon is inflated.

Clause 4: the balloon is inflatable through a lumen of the inner shaft that contains the guidewire.

Clause 5: a stiffening wire positioned radially between the inner shaft and the outer shaft.

Clause 6: the stent comprises: a radially expandable cylindrical frame comprising struts; and protruding features carried by one or more struts.

Clause 7: the stent is fixedly coupled to the inner shaft by an anchor portion that extends about at least a portion of the inner shaft.

Clause 8: the anchor portion is coupled to the inner shaft on a proximal side of the balloon.

Clause 9: the balloon comprises multiple segments at different axial positions along a length of the inner shaft, the multiple segments each being independently inflatable.

Clause 10: deflating the balloon; advancing the outer shaft over the stent; and removing the stent from the body lumen.

Clause 11: a connector at a proximal end of the inner shaft, the guidewire extending through the connector, the connector comprising a port in fluid communication with the balloon; and an outer shaft hub at a proximal end of the outer shaft, the inner shaft and the stabilizing wire extending through the outer shaft hub.

Clause 12: the target treatment site is a first target treatment site, the method further comprising before proximally retracting the outer shaft to further unsheath the stent, repositioning the stent to a second target treatment site.

Clause 13: the second length of the stent includes the first length of the stent.

Clause 14: before proximally retracting the outer shaft to further unsheath the stent, deflating the balloon and resheathing the stent.

Clause 15: before radially expanding the first length of the stent, locking the outer shaft relative to the inner shaft.

Clause 16: before radially expanding the second length of the stent, locking the outer shaft relative to the inner shaft.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. A system comprising:
   an outer shaft;

an inner shaft slidably disposed within the outer shaft and comprising a proximal portion, a distal portion, and an inflatable balloon on the proximal portion of the inner shaft;
a guidewire slidably disposed within the inner shaft; and
a stent slidably disposed within the outer shaft and on the distal portion of the inner shaft that is distal to the balloon, the stent being connected to a stabilizing wire that is slidably disposed within the outer shaft, wherein the stent comprises:
a radially expandable cylindrical frame comprising struts; and
protruding features carried by one or more struts.

2. The system of claim 1, further comprising:
a connector at a proximal end of the inner shaft, the guidewire extending through the connector, the connector comprising a port in fluid communication with the balloon; and
an outer shaft hub at a proximal end of the outer shaft, the inner shaft and the stabilizing wire extending through the outer shaft hub.

3. The system of claim 2, further comprising a locking member configured to lock the outer shaft hub to the inner shaft such that a position of the outer shaft relative to the inner shaft is maintained when the balloon is inflated.

4. The system of claim 2, further comprising incrementally spaced markers on the proximal portion of the inner shaft, wherein the outer shaft hub is slidable over the inner shaft along the proximal portion.

5. The system of claim 1, wherein the balloon is inflatable through a lumen of the inner shaft that contains the guidewire.

6. The system of claim 1, wherein the stent is fixedly coupled to the stabilizing wire by an anchor portion that extends about at least a portion of the stabilizing wire.

7. The system of claim 6, wherein the anchor portion is coupled to the inner shaft on a proximal side of the balloon.

8. The system of claim 1, further comprising a stiffening wire positioned radially between the inner shaft and the outer shaft.

9. The system of claim 1, wherein the balloon comprises multiple segments at different axial positions along a length of the inner shaft, the multiple segments each being independently inflatable.

10. A system comprising:
an outer shaft;
an inner shaft slidably disposed within the outer shaft and comprising an inflatable balloon on the inner shaft;
a guidewire slidably disposed within a lumen of the inner shaft, wherein the balloon is inflatable through the lumen of the inner shaft that contains the guidewire; and
a stent slidably disposed within the outer shaft and on a portion of the inner shaft, the stent being connected to a stabilizing wire that is slidably disposed within the outer shaft, wherein the stent comprises:
a radially expandable cylindrical frame comprising struts; and
protruding features carried by one or more struts.

11. The system of claim 10, wherein the stent is fixedly coupled to the stabilizing wire by an anchor portion that extends about at least a portion of the stabilizing wire.

12. The system of claim 10, further comprising a stiffening wire positioned radially between the inner shaft and the outer shaft.

13. The system of claim 10, wherein the balloon comprises multiple segments at different axial positions along a length of the inner shaft, the multiple segments each being independently inflatable.

14. A method comprising:
delivering over a guidewire an outer shaft ensheathing an inner shaft and a stent to a target treatment site within a body lumen of a patient, the guidewire being slidably disposed within the inner shaft, the stent being slidably disposed within the outer shaft and on a portion of the inner shaft that is distal to a balloon of the inner shaft the stent being connected to a stabilizing wire that is slidably disposed within the outer shaft;
proximally retracting the outer shaft to at least partially unsheathe the stent and the balloon;
moving the inner shaft distally relative to the stent until the stent is axially aligned with the balloon;
radially expanding the stent to an expanded state by expanding the balloon; and
piercing through a portion of a wall of the body lumen with one or more protruding features of the stent.

15. The method of claim 14, wherein during the delivering:
the guidewire is extending through a connector at a proximal end of the inner shaft, the connector comprising a port in fluid communication with the balloon; and
the inner shaft and the stabilizing wire are extending through an outer shaft hub at a proximal end of the outer shaft.

16. The method of claim 14, wherein the balloon is expanded by inflating the balloon through a lumen of the inner shaft that contains the guidewire.

17. The method of claim 14, wherein the stent comprises:
a radially expandable cylindrical frame comprising struts; and
the protruding features carried by one or more struts.

18. The method of claim 14, wherein the stent is fixedly coupled to the stabilizing wire by an anchor portion that extends about at least a portion of the stabilizing wire.

* * * * *